(12) United States Patent
Farritor et al.

(10) Patent No.: US 10,342,561 B2
(45) Date of Patent: Jul. 9, 2019

(54) QUICK-RELEASE END EFFECTORS AND RELATED SYSTEMS AND METHODS

(71) Applicant: Board of Regents of the University of Nebraska, Lincoln, NE (US)

(72) Inventors: Shane Farritor, Lincoln, NE (US); Jeff Shasho, Brooklyn, NY (US); Alan Bachman, Milford, CT (US); Kenneth Blier, Cheshire, CT (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 951 days.

(21) Appl. No.: 14/853,477

(22) Filed: Sep. 14, 2015

(65) Prior Publication Data

US 2016/0074120 A1    Mar. 17, 2016

Related U.S. Application Data

(60) Provisional application No. 62/049,419, filed on Sep. 12, 2014.

(51) Int. Cl.
    *A61B 17/29*    (2006.01)
    *A61B 34/30*    (2016.01)
    *A61B 17/00*    (2006.01)

(52) U.S. Cl.
    CPC .......... *A61B 17/2909* (2013.01); *A61B 17/29* (2013.01); *A61B 34/30* (2016.02);
    (Continued)

(58) Field of Classification Search
    CPC .............. A61B 17/2909; A61B 17/292; A61B 2017/2912; A61B 2017/0046;
    (Continued)

(56) References Cited

U.S. PATENT DOCUMENTS 3,870,264 A    3/1975    Robinson
3,989,952 A    11/1976   Timberlake et al.
(Continued)

FOREIGN PATENT DOCUMENTS

CN    1082821918    12/2012
DE    102010040405  3/2012
(Continued)

OTHER PUBLICATIONS

Palm, William, "Rapid Prototyping Primer" May 1998 (revised Jul. 30, 2002) (http://www.me.psu.edu/lamancusa/rapidpro/primer/chapter2.htm).
(Continued)

*Primary Examiner* — Katherine M Rodjom
(74) *Attorney, Agent, or Firm* — Davis, Brown, Koehn, Shors & Roberts, P.C.; Sean D. Solberg

(57) ABSTRACT

The various embodiments disclosed herein relate to arms or forearms of medical devices that are configured to couple with quick-release end effectors, quick-release end effectors for use with such medical devices, and arms or forearms coupled to such quick-release end effectors. Certain forearms and end effectors have magnetic couplings, while others have mechanical couplings, and further implementations have both magnetic and mechanical couplings.

14 Claims, 10 Drawing Sheets

(52) U.S. Cl.
CPC .............. *A61B 2017/00398* (2013.01); *A61B 2017/00473* (2013.01); *A61B 2017/00477* (2013.01); *A61B 2017/00876* (2013.01)

(58) Field of Classification Search
CPC ........... A61B 2017/00473; A61B 2017/00477; A61B 34/30; A61B 18/1442; A61B 18/1447
See application file for complete search history.

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,579,476 A * | 4/1986 | Post .................. F16D 1/116 403/322.2 |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,522,669 A * | 6/1996 | Recker .................. F16B 21/165 403/325 |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,913,874 A * | 6/1999 | Berns ................... A61B 17/295 606/205 |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |

(56) References Cited

U.S. PATENT DOCUMENTS

| | | |
|---|---|---|
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |

(56) References Cited

U.S. PATENT DOCUMENTS

| | | |
|---|---|---|
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267254 A1 * | 12/2004 | Manzo .................. A61B 18/14 606/39 |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Khalili et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |

(56) References Cited

U.S. PATENT DOCUMENTS

| | | |
|---|---|---|
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |
| 2013/0345717 A1 | 5/2013 | Scarfogliero et al. |
| 2014/0001234 A1* | 1/2014 | Shelton, IV ..... A61B 17/07207 227/176.1 |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| KR | 20100029087 A | 3/2010 |
| WO | WO 1992/21291 | 5/1991 |
| WO | 9610957 A1 | 4/1996 |
| WO | 9639944 A1 | 12/1996 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | 2009014917 A2 | 1/2009 |
| WO | WO 2009/144729 | 12/2009 |
| WO | WO2010/042611 | 4/2010 |
| WO | WO2010/046823 | 4/2010 |
| WO | WO201050771 A2 | 5/2010 |
| WO | WO 2011/118646 A1 | 9/2011 |
| WO | WO 2011/135503 A1 | 11/2011 |
| WO | WO 2011135503 | 11/2011 |
| WO | WO 2011075693 | 7/2012 |
| WO | WO 2013009887 | 1/2013 |
| WO | WO 2014011238 | 1/2014 |

OTHER PUBLICATIONS

International Preliminary Report on Patentability from related case PCT/US2007/014567, dated Jan. 8, 2009, 11 pp.
International Search report and Written Opinion from international application No. PCT/US2012/41911, dated Mar. 13, 2013.
International Search Report and Written Opinion from international application No. PCT/US12/46274, dated Sep. 25, 2012.
International Search Report and Written Opinion from international application No. PCT/US2007/089191, dated Nov. 10, 2008, 20 pp.
"International Search Report and Written Opinion from international application No. PCT/US07/14567, dated Apr. 28, 2008, 19 pp."
International Search Report and Written Opinion of international application No. PCT/US2008/069822, dated Aug. 5, 2009, 12 pp.
International Search Report and Written Opinion of international application No. PCT/US2008/073334, dated Jan. 12, 2009, 11 pp.
International Search Report and Written Opinion of international application No. PCT/US2008/073369, dated Nov. 12, 2008, 12 pp.
International Search Report and Written Opinion issued in PCT/US11/46809, dated Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coll. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.

(56) References Cited

OTHER PUBLICATIONS

Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L, Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.

(56) References Cited

OTHER PUBLICATIONS

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May, 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy A Breakthrough Diagnostic Tool for Small Intestine Imagining," vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al., "The development and application of wireless capsule endoscopy," Int. J. Med. Robot. Comput. Assist. Surgery, 2004; I (1): 114-123.
Gong et al., "Wireless endoscopy," Gastrointestinal Endoscopy 2000; 51(6): 725-729.
Hanly et al., "Value of the SAGES Learning Center in introducing new technology," Surgical Endoscopy, 2004; 19(4): 477-483.
Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.

(56) References Cited

OTHER PUBLICATIONS

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

Rentschler et al., Mobile In Vivo Biopsy Robot, IEEE International Conference on Robotics and Automation, Orlando, Florida, May 2006, pp. 4155-4160.

Rentschler et al., "Miniature in vivo Robots for Remote and Harsh Environments," IEEE Transactions on Information Technology in Biomedicine, Jan. 2006; 12(1): 66-75.

Rentschler et al., "An In Vivo Mobile Robot for Surgical Vision and Task Assistance," Journal of Medical Devices, Mar. 2007, vol. 1: 23-29.

Rentschler et al., "In vivo Mobile Surgical Robotic Task Assistance," 1 pg.

Rentschler et al., "In vivo Robotics during the NEEMO 9 Mission," Medicine Meets Virtual Reality, Feb. 2007, I pg.

Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.

Rentschler et al., "Mechanical Design of Robotic In Vivo Wheeled Mobility," ASME Journal of Mechanical Design, 2006a, pp. I-II.

Rentschler et al., "Mobile In Vivo Camera Robots Provide Sole Visual Feedback for Abdominal Exploration and Cholecystectomy," Journal of Surgical Endoscopy, 20-I: 135-138, 2006b.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled Robotic Mobility," IEEE Transactions on Robotics, 22 (2): 308-321, 2005c.

Rentschler et al., "Natural Orifice Surgery with an Endoluminal Mobile Robot," The Society of American Gastrointestinal Endoscopic Surgeons, Dallas, TX, Apr. 2006d, 14 pp.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.

Rentschler et al., "Toward In Vivo Mobility," Studies in Health Technology and Infornnatics—Medicine Meets Virtual Reality, ISO Press, Long Beach, CA, 2005a, III: 397-403.

Response to Rule 312 Amendment in related case U.S. Appl. No. 11/695,944, dated Jan. 12, 2009, 2 pp.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.

Rosen et al., "Objective Laparoscopic Skills Assessments of Surgical Residents Using Hidden Markov Models Based on Haptic Information and Tool/Tissue Interactions," Studies in Health Technology and Infornnatics—Medicine Meets Virtual Reality, Jan. 2001, 7 pp.

Rosen et al., "Spherical Mechanism Analysis of a Surgical Robot for Minimally Invasive Surgery—Analytical and Experimental Approaches," Studies in Health Technology and Infornnatics—Medicine Meets Virtual Reality, pp. 442-448, Jan. 2005.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Robot-Assisted surgical systems: a new era in laparoscopic surgery," Ann R. Coll Surg Engl., 2002; 84: 223-226.

Ruurda et al., "Feasibility of Robot-Assisted Laparoscopic Surgery," Surgical Laparoscopy, Endoscopy & Percutaneous Techniques, 2002; 12(1):41-45.

Sackier et al., "Robotically assisted laparoscopic surgery," Surgical Endoscopy, 1994; 8: 63-66.

Salky, "What is the Penetration of Endoscopic Techniques into Surgical Practice?" Digestive Surgery, 2000; 17:422-426.

Satava, "Surgical Robotics: The Early Chronicles," Surgical Laparoscopy, Endoscopy & Percutaneous Techniques, 2002; 12(1): 6-16.

Schippers et al., (1996) "Requirements and Possibilities of Computer-Assisted Endoscopic Surgery," In: Computer Integrated Surgery: Technology and Clinical Applications, pp. 561-565.

Schurr et al., "Robotics and Telemanipulation Technologies for Endoscopic Surgery," Surgical Endoscopy, 2000; 14: 375-381.

Schwartz, "In the Lab: Robots that Slink and Squirm," The New York Times, Mar. 27, 2007, 4 pp.

Sharp LL-151-3D, http://www.sharp3d.com, 2006, 2 pp.

Slatkin et al., "The Development of a Robotic Endoscope," Proceedings of the 1995 IEEE International Conference on Robotics and Automation, pp. 162-171, 1995.

Smart Pill "Fastastic Voyage: Smart Pill to Expand Testing," http://www.smartpilldiagnostics.com, Apr. 13, 2005, 1 pg.

Southern Surgeons Club (1991), "A prospective analysis of 1518 laparoscopic cholecystomies," N. Eng. 1 Med. 324 (16): 1073-1078.

Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.

Stiff et al.., "Long-term Pain: Less Common After Laparoscopic than Open Cholecystectomy," British Journal of Surgery, 1994; 81: 1368-1370.

Strong, et al., "Efficacy of Novel Robotic Camera vs. a Standard Laproscopic Camera," Surgical Innovation vol. 12, No. 4, Dec. 2005, Westminster Publications, Inc., pp. 315-318.

Suzumori et al., "Development of Flexible Microactuator and its Applications to Robotics Mechanisms," Proceedings of the IEEE International Conference on Robotics and Automation, 1991: 1622-1627.

Taylor et al., "A Telerobotic Assistant for Laparoscopic Surgery," IEEE Eng Med Biol, 1995; 279-287.

Tendick et al.. (1993), "Sensing and Manipulation Problems in Endoscopic Surgery: Experiment, Analysis, and Observation," Presence 2( 1): 66-81.

Stoianovici et al., "Robotic Tools for Minimally Invasive Urologic Surgery", Jan. 1, 2002, pp. 1-17.

Cleary et al., "State of the Art in Surgical Rootics: Clinical Applications and Technology Challenges", "Computer Aided Surgery", Jan. 1, 2002, pp. 312-328, vol. 6.

Green, "Telepresence Surgery", Jan. 1, 1995, Publisher: IEEE Engineering in Medicine and Biology.

* cited by examiner

QUICK-RELEASE END EFFECTORS AND RELATED SYSTEMS AND METHODS

CROSS-REFERENCE TO RELATED APPLICATION

This application claims the benefit under 35 U.S.C. § 119(e) to U.S. Provisional Application 62/049,419, filed Sep. 12, 2014 and entitled "Quick-Release End Effectors and Related Systems and Methods," which is hereby incorporated herein by reference in its entirety.

FIELD OF THE INVENTION

The various embodiments disclosed herein relate to various medical device systems and related components, including robotic and/or in vivo medical devices and related components. More specifically, certain embodiments include various medical device operational components, often referred to as "end effectors." Certain end effector embodiments disclosed herein relate to quick-release end effectors that can be easily coupled to and removed from a medical device—including the forearm of a robotic medical device—with ease and efficiency. Further embodiments relate to systems and methods for operating the above components.

BACKGROUND OF THE INVENTION

Invasive surgical procedures are essential for addressing various medical conditions. When possible, minimally invasive procedures, such as laparoscopy, are preferred. However, known minimally invasive technologies such as laparoscopy are limited in scope and complexity due in part to the need to remove and insert new surgical tools into the body cavity when changing surgical instruments due to the size of the access ports. Known robotic systems such as the da Vinci® Surgical System (available from Intuitive Surgical, Inc., located in Sunnyvale, Calif.) are also restricted by the access ports and trocars, the necessity for medical professionals to remove and insert new surgical tools into the abdominal cavity, as well as having the additional disadvantages of being very large, very expensive, unavailable in most hospitals, and having limited sensory and mobility capabilities.

Various robotic surgical tools have been developed to perform certain procedures inside a target cavity of a patient. These robotic systems are intended to replace the standard laparoscopic tools and procedures—such as, for example, the da Vinci® system—that involve the insertion of long surgical tools through trocars positioned through incisions in the patient such that the surgical tools extend into the target cavity and allow the surgeon to perform a procedure using the long tools. As these systems are developed, various new components are developed to further improve the operation and effectiveness of these systems.

There is a need in the art for improved end effectors for use with medical devices, including robotic surgical systems.

BRIEF SUMMARY OF THE INVENTION

Discussed herein are various arms or forearms of medical devices that are configured to receive quick-release end effectors. Further embodiments relate to such quick-release end effectors. Additional implementations relate to arms or forearms of medical devices coupled to such quick-release end effectors.

In Example 1, an arm component for a medical device comprises an arm body, a rotatable cylinder disposed within the arm body, and a rotatable linear drive component operably coupled to the rotatable cylinder. The rotatable cylinder comprises a fluidically sealed end effector lumen defined within the rotatable cylinder and at least one torque transfer channel defined in a wall of the end effector lumen. The rotatable linear drive component comprises a rotatable body, and a drive component lumen defined in a distal portion of the rotatable body, wherein the drive component lumen comprises mating features defined within the drive component lumen.

Example 2 relates to the arm component according to Example 1, further comprising a ring seal disposed between the arm body and the rotatable cylinder.

Example 3 relates to the arm component according to Example 1, further comprising a first motor operably coupled to a first drive gear, wherein the first drive gear is operably coupled to an external gear disposed on an outer wall of the rotatable cylinder, wherein actuation of the first motor causes rotation of the rotatable cylinder.

Example 4 relates to the arm component according to Example 1, further comprising a second motor operably coupled to a second drive gear, wherein the second drive gear is operably coupled to a driven gear operably coupled to the linear drive component, wherein actuation of the second motor causes rotation of the linear drive component.

Example 5 relates to the arm component according to Example 1, further comprising a first outer contact ring disposed around the rotatable cylinder, a second outer contact ring disposed around the rotatable cylinder, a first contact component disposed on an outer wall of the rotatable cylinder such that the first contact component is in continuous contact with the first inner contact ring regardless of a rotational position of the rotatable cylinder, a second contact component disposed on the outer wall of the rotatable cylinder such that the second contact component is in continuous contact with the second inner contact ring regardless of the rotational position of the rotatable cylinder, a first inner contact ring disposed on the inner wall of the end effector lumen, and a second inner contact ring disposed on the inner wall of the end effector lumen.

Example 6 relates to the arm component according to Example 5, further comprising a quick-release end effector configured to be positionable within the end effector lumen, the quick-release end effector comprising first and second end effector contact components, wherein the first end effector contact component is in contact with the first inner contact ring and the second end effector contact component is in contact with the second inner contact ring when the quick-release end effector is operably coupled to the arm.

Example 7 relates to the arm component according to Example 1, further comprising a quick-release end effector configured to be positionable within the end effector lumen. The quick-release end effector comprises an end effector body, at least one torque transfer protrusion defined in an exterior portion of the end effector body, a rod disposed within the end effector body, and a rod coupling component disposed at a proximal portion of the rod. The at least one torque transfer protrusion is configured to be mateable with the at least one torque transfer channel in the end effector lumen. The rod coupling component is configured to be coupleable with the mating features defined in the lumen of the rotatable linear drive component.

In Example 8, a quick-release end effector for a medical device comprises an end effector body, an end effector coupling component disposed around the end effector body, at least one torque transfer protrusion defined in an exterior portion of the end effector body, a rod disposed within the end effector body, a rod coupling component disposed at a proximal portion of the rod, and first and second contact rings disposed around the rod. The end effector coupling component comprises at least one male protrusion extending from the coupling component. The rod coupling component comprising first mating features disposed on an external portion of the rod coupling component.

Example 9 relates to the quick-release end effector according to Example 8, further comprising an end effector disposed at a distal end of the end effector body, wherein the end effector is operably coupled to the rod such that actuation of the rod causes actuation of the end effector.

Example 10 relates to the quick-release end effector according to Example 8, further comprising a grasper end effector comprising first and second grasper arms, wherein the first contact ring is electrically coupled to the first grasper arm and the second contact ring is electrically coupled to the second grasper arm.

Example 11 relates to the quick-release end effector according to Example 8, wherein the end effector is configured to be positionable in a lumen of an arm of a medical device.

Example 12 relates to the quick-release end effector according to Example 8, wherein the end effector is configured to be positionable in a lumen of an arm of a medical device, the lumen comprising at least one torque transfer channel defined in the lumen, wherein the at least one torque transfer protrusion is configured to be mateable with the at least one torque transfer channel in the end effector lumen.

Example 13 relates to the quick-release end effector according to Example 8, wherein the end effector is configured to be positionable in a lumen of an arm of a medical device, wherein the arm comprises at least one female channel defined in a distal portion of the arm, wherein the end effector coupling component is configured to be coupleable to the arm such that the at least one male protrusion is mateable with the at least one female channel.

Example 14 relates to the quick-release end effector according to Example 8, wherein the end effector is configured to be positionable in an arm of a medical device. The arm comprises an arm body, a rotatable cylinder disposed within the arm body, and a rotatable linear drive component operably coupled to the rotatable cylinder. The rotatable cylinder comprises an end effector lumen defined within the rotatable cylinder, and at least one torque transfer channel defined in a wall of the end effector lumen. The linear drive component comprises a rotatable body, and a lumen defined in a distal portion of the rotatable body, wherein the lumen comprises second mating features defined within the lumen. The first mating features of the rod coupling component are configured to be coupleable with the second mating features defined within the lumen of the rotatable linear drive component.

In Example 15, an arm component for a medical device comprises a forearm and a quick-release end effector. The forearm comprises a forearm body, a fluidically sealed tube defining an end effector lumen within the forearm body, a magnetic ring disposed around the end effector lumen, and a linear drive component disposed at a proximal end of the end effector lumen. The linear drive component comprises a proximal section comprising external threads and a slot defined in a distal portion of the linear drive component. The quick-release end effector is configured to be positionable within the end effector lumen and comprises an end effector body, a magnetic collar disposed around the end effector body, a rod disposed within the end effector body, and at least one finger component operably coupled to the rod, wherein the at least one finger component extends proximally from the rod and is configured to be coupleable with the slot in the linear drive component.

Example 16 relates to the arm component for a medical device according to Example 15, further comprising a first motor operably coupled to a first drive gear, wherein the first drive gear is operably coupled to a first driven gear, wherein the driven gear is operably coupled to the magnetic ring, wherein actuation of the first motor causes rotation of the magnetic ring.

Example 17 relates to the arm component for a medical device according to Example 16, wherein the magnetic collar is magnetically coupleable with the magnetic ring such that rotation of the magnetic ring causes rotation of the magnetic collar.

Example 18 relates to the arm component for a medical device according to Example 15, further comprising a second motor operably coupled to a second drive gear, wherein the second drive gear is operably coupled to a drive cylinder, wherein the drive cylinder is operably coupled to the proximal section of the linear drive component, wherein the actuation of the second motor causes axial movement of the linear drive component.

Example 19 relates to the arm component for a medical device according to Example 15, wherein the fluidically sealed tube is fixedly coupled to the linear drive component, wherein the fluidically sealed tube is configured to flex when the linear drive component moves axially.

Example 20 relates to the arm component for a medical device according to Example 15, further comprising a compression spring disposed within the forearm body, wherein the compression spring is operably coupled to the forearm body and the at least one finger.

In Example 21, an arm component for a medical device comprises a forearm comprising a forearm body, a fluidically sealed tube defining an end effector lumen within the forearm body, a first magnetic ring disposed around the end effector lumen at or near the distal end of the forearm body, a first motor operably coupled to a first drive gear, a second magnetic ring disposed around the end effector lumen at or near a proximal end of the forearm body, and a second motor operably coupled to a second drive gear. The lumen comprises an opening defined at a distal end of the forearm body. The first drive gear is operably coupled to a first driven gear, wherein the first driven gear is operably coupled to the first magnetic ring. The second drive gear is operably coupled to a second driven gear, wherein the second driven gear is operably coupled to the second magnetic ring.

In Example 22, an arm component for a medical device comprises a forearm and a quick-release end effector. The forearm comprises a forearm body, a rotatable cylinder disposed within the forearm body, a linear drive component operably coupled to the rotatable cylinder, and a rotatable drive component defining a drive component lumen comprising internal threads. The rotatable cylinder comprises an end effector lumen defined within the rotatable cylinder. The linear drive component comprises a proximal section comprising external threads, a lumen defined in a distal portion of the linear drive component, and a cylinder coupling pin coupled to the linear drive component. The lumen comprises a hook coupling pin disposed within the lumen. Each end of the cylinder coupling pin is slideably disposed in a longitudinal slot defined in the rotatable cylinder. The drive component lumen is configured to be threadably coupled to the proximal section of the linear drive component. The quick-release end effector is configured to be positionable within the end effector lumen and comprises an end effector body, a rod disposed within the end effector body, and a coupling hook operably coupled to a proximal portion of the rod, wherein the coupling hook extends proximally from the rod and is configured to be coupleable with the hook coupling pin.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various systems and devices disclosed herein relate to devices for use in medical procedures and systems. More specifically, various embodiments relate to end effector components or devices that can be used in various procedural devices and systems. For example, certain embodiments relate to quick-release end effector components incorporated into or used with various medical devices, including robotic and/or in vivo medical devices. It is understood that the term "quick-release" as used herein are intended to describe any end effector, forearm, or combination thereof that can be easily and/or quickly coupled and/or uncoupled by anyone in the surgical theater, including any nurse or assistant (in contrast to a component that cannot be coupled or uncoupled quickly or easily or requires someone with technical expertise).

Figure 1A:
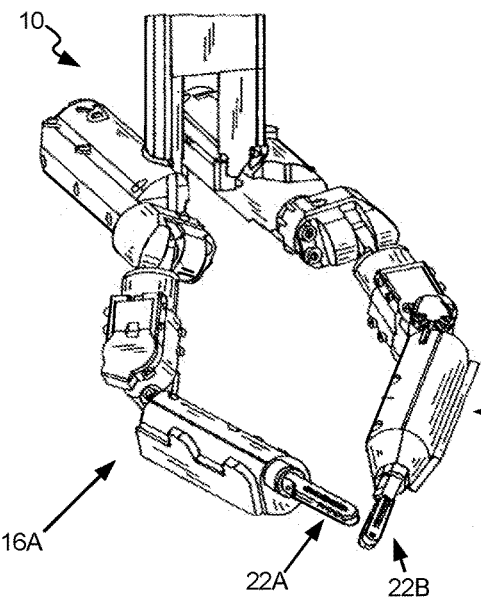
FIG. 1A is a perspective view of a robotic surgical device having arms.
Figure 1B:
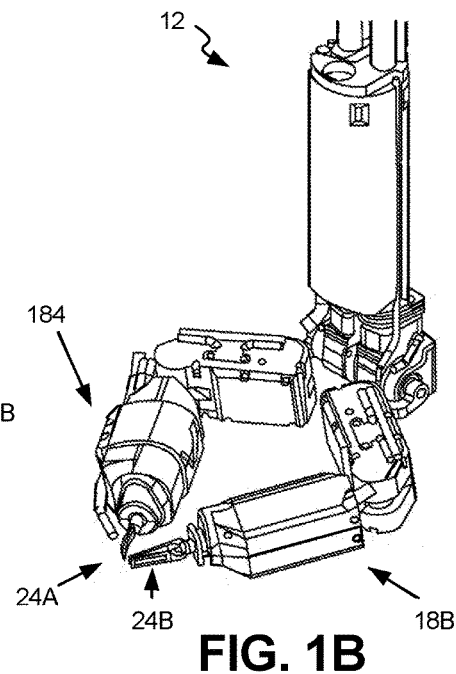
FIG. 1B is a perspective view of another robotic surgical device having arms.
Figure 1C:
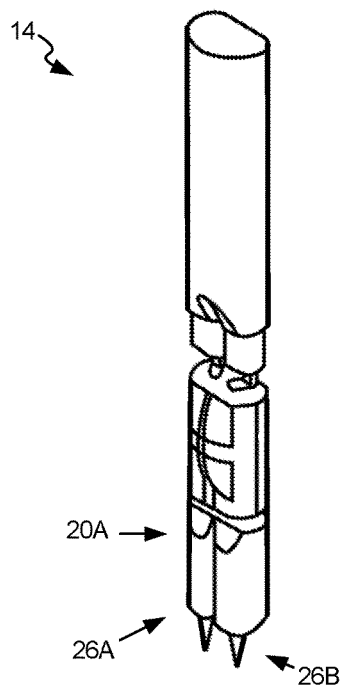
FIG. 1C is a perspective view of a further robotic surgical device having arms.
Figure 1D:
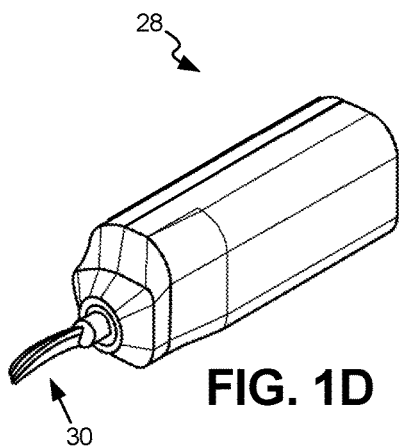
FIG. 1D is a perspective view of a forearm of a robotic surgical device having a quick-release end effector, according to one embodiment.

It is understood that the various embodiments of end effector devices or components disclosed herein can be incorporated into or used with any other known medical devices, systems and methods, including, but not limited to, robotic or in vivo devices as defined herein. For example, FIGS. 1A-1D depict certain exemplary medical devices and systems that could incorporate a quick-release end effector as disclosed or contemplated herein. More specifically, FIGS. 1A-1C show robotic surgical devices 10, 12, 14 having arms 16A, 16B, 18A, 18B, 20A, 20B to which certain end effectors 22A, 22B, 24A, 24B, 26A, 26B have been coupled. In one implementation, the end effectors 22A, 22B, 24A, 24B, 26A, 26B are quick-release end effectors as disclosed herein. Further, FIG. 1D depicts a forearm 28 that has a quick-release end effector 30.

As a further example, the various embodiments disclosed herein can be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966, 741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192, 663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), Ser. No. 13/738,706 (filed Jan. 10, 2013 and entitled "Methods, Systems, and Devices for Surgical Access and Insertion"), Ser. No. 13/833,605 (filed Mar. 15, 2013 and entitled "Robotic Surgical Devices, Systems, and Related Methods"), Ser. No. 13/839,422 (filed Mar. 15, 2013 and entitled "Single Site Robotic Devices and Related Systems and Methods"), Ser. No. 13/834,792 (filed Mar. 15, 2013 and entitled "Local Control Robotic Surgical Devices and Related Methods"), Ser. No. 14/208,515 (filed Mar. 13, 2014 and entitled "Methods, Systems, and Devices Relating to Robotic Surgical Devices, End Effectors, and Controllers"), Ser. No. 14/210,934 (filed Mar. 14, 2014 and entitled "Methods, Systems, and Devices Relating to Force Control Surgical Systems), Ser. No. 14/212,686 (filed Mar. 14, 2014 and entitled "Robotic Surgical Devices, Systems, and Related Methods"), and Ser. No. 14/334,383 (filed Jul. 17, 2014 and entitled "Robotic Surgical Devices, Systems, and Related Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

In accordance with certain exemplary embodiments, any of the various embodiments disclosed herein can be incorporated into or used with a natural orifice translumenal endoscopic surgical device, such as a NOTES device. Those skilled in the art will appreciate and understand that various combinations of features are available including the features disclosed herein together with features known in the art.

Certain device implementations disclosed in the applications listed above can be positioned within or into a body cavity of a patient, including certain devices that can be positioned against or substantially adjacent to an interior cavity wall, and related systems. An "in vivo device" as used herein means any device that can be positioned, operated, or controlled at least in part by a user while being positioned into or within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Further, the various end effector embodiments could be incorporated into various robotic medical device systems that are actuated externally, such as those available from Apollo Endosurgery, Inc., Hansen Medical, Inc., Intuitive Surgical, Inc., and other similar systems, such as any of the devices disclosed in the applications that are incorporated herein elsewhere in this application. Alternatively, the various end effector embodiments can be incorporated into any medical devices that use end effectors.

Figure 2:
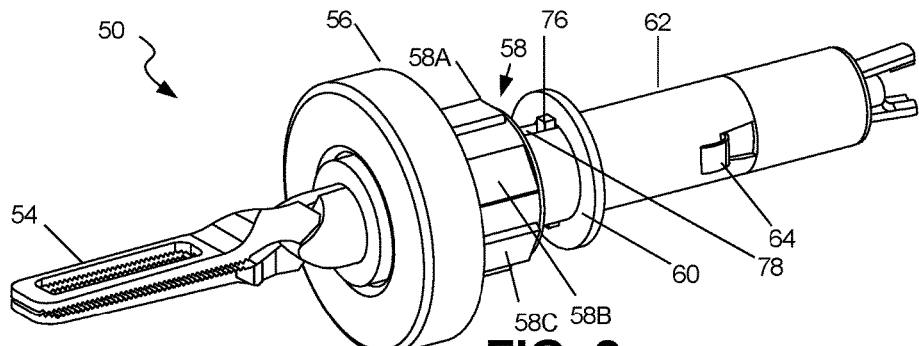
FIG. 2 is a perspective view of a quick-release end effector, according to one embodiment.
Figure 3A:
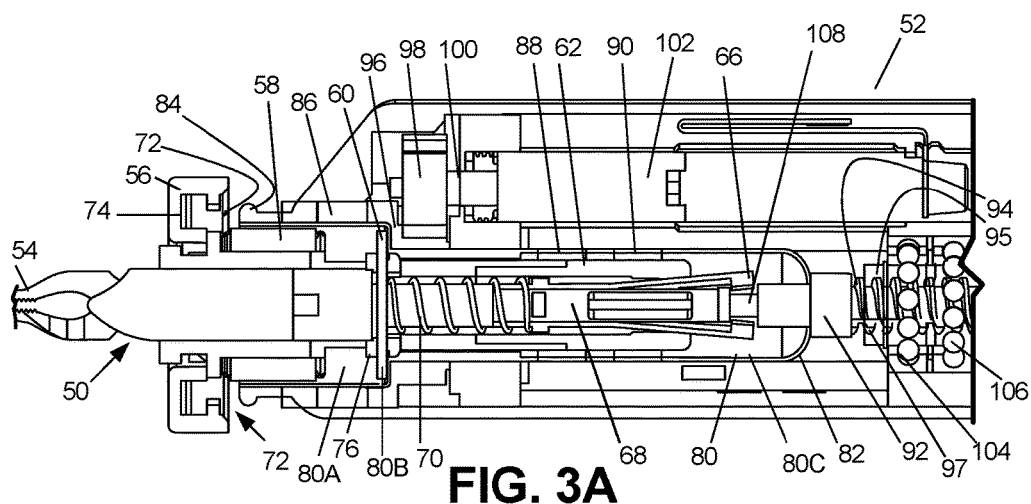
FIG. 3A is an expanded cross-sectional side view of a portion of the quick-release end effector of FIG. 2 positioned in a portion of a forearm, according to one embodiment.
Figure 3B:
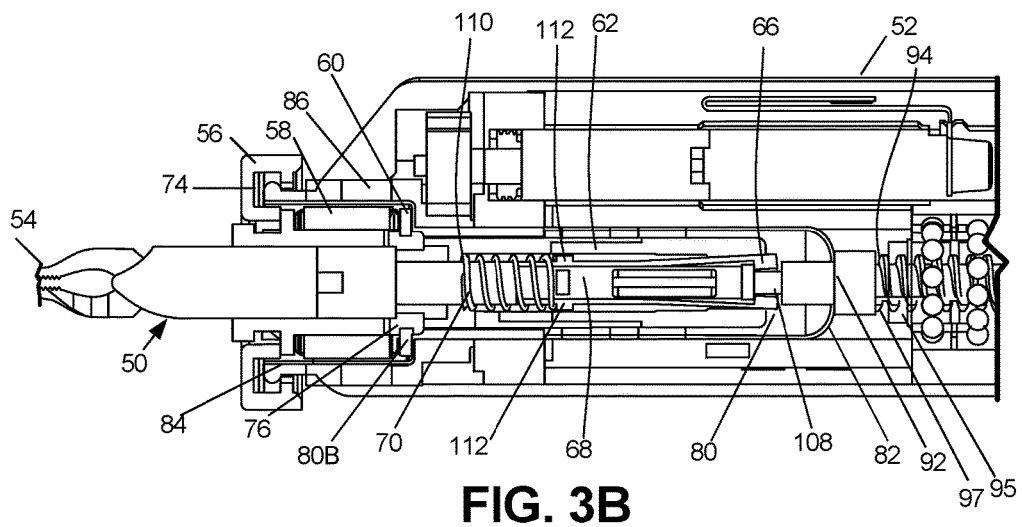
FIG. 3B is a further expanded cross-sectional side view of the portion of the quick release end effector positioned in the portion of the forearm of FIG. 3A.
Figure 4A:
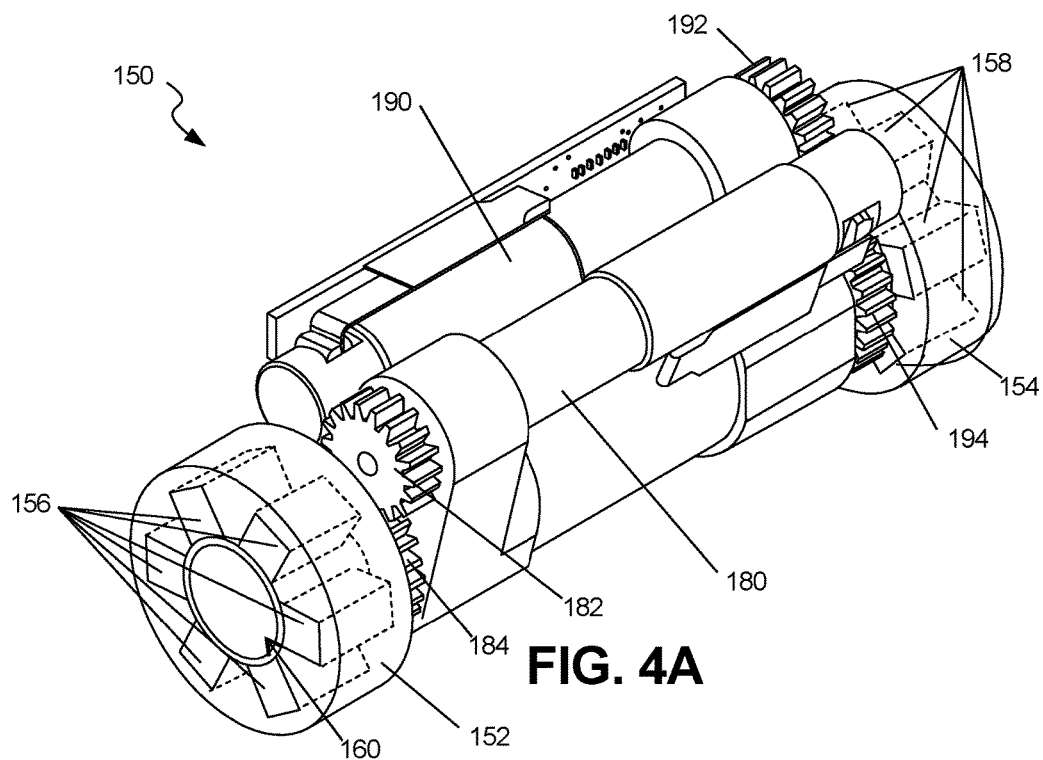
FIG. 4A is a perspective view of a quick-release forearm configured to receive a quick-release end effector, according to another embodiment.
Figure 4B:
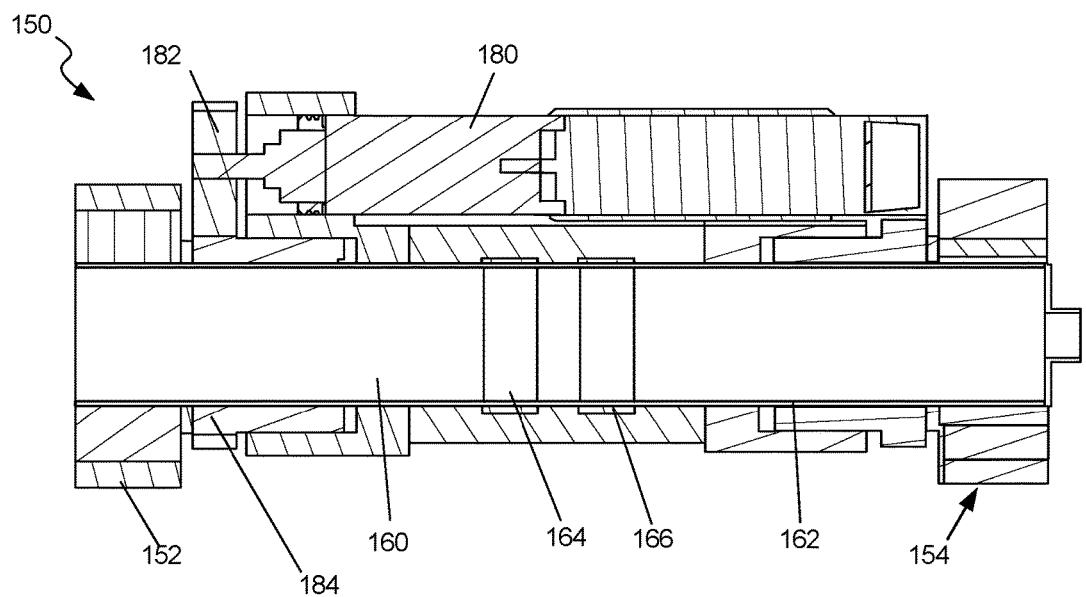
FIG. 4B is a cross-sectional side view of the quick-release forearm of FIG. 4A.
Figure 4C:
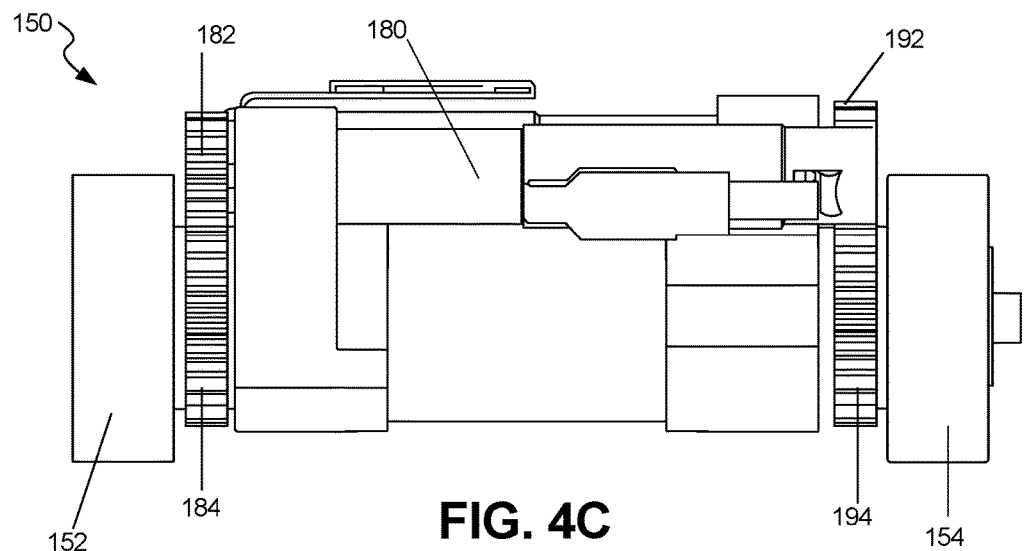
FIG. 4C is a side view of the quick-release forearm of FIG. 4A.
Figure 4D:
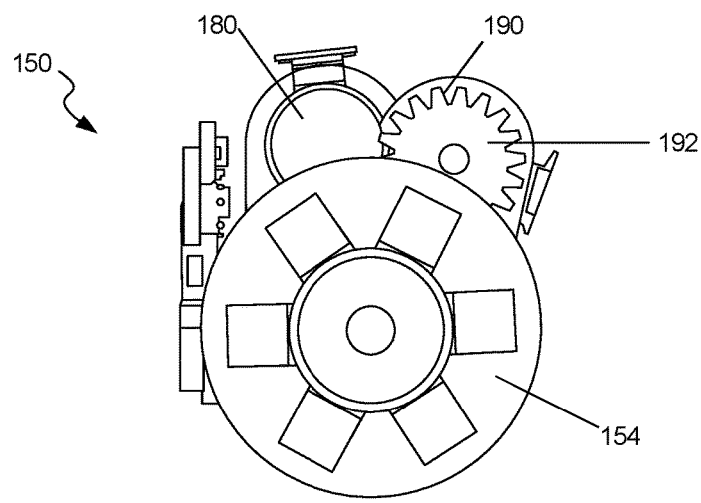
FIG. 4D is an end view of the quick-release forearm of FIG. 4A.

FIGS. 2-3B depict a quick-release, magnetically-coupled end effector 50 that is releaseably coupleable to forearm 52, according to one embodiment. As best shown in FIG. 2, the end effector 50 in this implementation has a grasper 54. As best shown in FIGS. 2 and 3A, the end effector 50 also has a mateable coupler 56, a magnetic collar 58, a disk 60, a central rod 68, a body (also referred to herein as a "forearm body") 62 that is a slidable cylinder 62 slidably disposed over the rod 68, a compression spring 70 disposed within the cylinder 62 and over the rod 68, two leaf springs (one leaf spring 64 is visible in FIG. 2, while the second leaf spring is positioned on the other side of the cylinder 62 and thus not shown in the figure), and coupling fingers (also referred to as "finger components" or "coupling components") 66. As best shown in FIGS. 3A and 3B, the mateable coupler 56 has an opening 72 on its proximal side that is configured to receive and be mateable with the coupling projection 84 on the distal end of the forearm 52 (discussed further below). The opening 72 according to one embodiment can contain an o-ring 74 as best shown in FIGS. 3A and 3B that can maintain a sealed connection between the coupler 56 and the projection 84 of the forearm 52. In one implementation, the magnetic collar 58 is made up of multiple magnets 58A, 58B, 58C as shown that are positioned on the collar around the full circumference of the end effector 50.

The disk 60 is fixedly coupled to the central rod 68 via a connection tab 76 that is positioned in a slot 78 (as best shown in FIG. 2) in the slidable cylinder 62 such that the cylinder 62 is slidable in relation to the disk 60 as well as the central rod 68. As such, the disk 60, as will be described in further detail below, can serve as an axial constraint during insertion of the end effector 50 into the forearm 52 and as a bearing during rotation of the end effector 50 in relation to the forearm 52.

The first leaf spring 64 is electrically connected to one of the blades of the grasper 54 via a wire or other electrical connection (not shown), while the second leaf spring (not shown) is electrically connected to the other of the two blades of the grasper 54 in the same or a similar fashion. In this implementation, the blades of the grasper 54 are electrically isolated from each other. As such, the graspers 54 can be a cautery tool with electrical energy being transferred to the grasper 54 blades via the leaf springs 64, not shown, as explained in further detail below.

The two finger components 66 are positioned on opposite sides of the central rod 68 and are attached to the rod 68 at the distal end of the fingers 66 (or along a distal portion of the FIGS. 66) such that the fingers 66 do not move axially in relation to the rod 68. The proximal ends of the fingers 66 extend proximally farther than the rod 68 and are not coupled to the rod at their proximal ends, thereby allowing the proximal ends of the fingers 66 to be capable of extending radially away from the rod 68. The cylinder 62 is slidable laterally along the length of the end effector 50, and more specifically along the length of the central rod 68, such that the cylinder 62 can operate in combination with the coupler 56 and the coupling fingers 66 as will be discussed in further detail below to couple the end effector 50 to the forearm 52.

In one implementation, the forearm 52 has an end effector lumen 80 defined by a fluidically impervious tube 82 such that the lumen 80 is fluidically sealed. As a result, the internal components of the forearm 52 are fluidically sealed off from any fluids present in the lumen 80. As such, the lumen 80 is capable of receiving an end effector (such as end effector 50) while maintaining a complete fluidic or hermetic seal between the lumen 80 (and any fluids in the lumen 80) and the interior portions of the forearm 52. In this implementation, the fluidic seal created by the tube 82 makes it possible to quickly remove and replace any end effector (such as end effector 50) without risking contamination of the interior components of the forearm 52.

The lumen 80, in one embodiment, has a shoulder 80B that separates a larger diameter portion 80A from a smaller diameter portion 80C. The tube 82 is positioned in the lumen 80 such that the tube 82 defines the lumen 80. In one implementation, the tube 82 is fixedly coupled or affixed to the linear drive component 92 at a proximal end of the tube 82 as best shown in FIG. 3A. In accordance with one embodiment, the tube 82 is made of a flexible material such that when the linear drive component 92 is moved laterally as described below, the tube 82 remains attached to the drive component 92 and simply flexes or deforms to accommodate the movement of the drive component 92.

Further, the forearm 52 has a coupling projection 84 (discussed above), a magnetic ring 86, and two contact rings 88, 90. In addition, the forearm 52 has a linear drive component 92 that has a threaded proximal shaft 94 and a slot 108 defined in a distal portion of the component 92. Alternatively, the threaded shaft 94 is a separate component operably coupled to the linear drive component 92. The forearm 52 also has a drive cylinder 95 having a threaded lumen (not shown) through which the threaded shaft 94 is positioned such that the threaded shaft 94 is threadably coupled to the drive cylinder 95. In addition, two bearings 104, 106 are disposed around the drive cylinder 95 such that the drive cylinder 95 is rotatably positioned within the bearings 104, 106.

Each of the contact rings 88, 90 is positioned around the wall of the tube 82 of the lumen 80 such that each ring 88, 90 encircles the lumen 80. One of the contact rings 88, 90 is positioned along the length of the lumen 80 such that it is in contact with the leaf spring 64 when the end effector 50 is coupled to the forearm 52 as shown in FIG. 3B, while the other of the two contact rings 88, 90 is positioned such that it is in contact with the other leaf spring (not shown). In this configuration, once the end effector 50 is coupled to the forearm 52, the leaf springs (64, not shown) are continuously in contact with the contact rings 88, 90, even when the forearm body 62 is rotating. Further, each of the contact rings 88, 90 is operably coupled to a separate wire (not shown) that extends to an electrical energy source (such as a cautery generator, for example) such that electrical energy can be transmitted from the power sources to the rings 88, 90 and—via the contact between the rings 88, 90 and the leaf springs (64, not shown)—to the leaf springs (64, not shown), and thereby to the grasper 54 blades. As a result, the grasper 54 can be a bipolar cautery tool. Alternatively, the end effector 50 can also be a monopolar cautery tool if the same electrical energy is supplied to both contact rings 88, 90. In fact, as will be discussed specifically with certain of the additional embodiments below, every forearm implementation disclosed or contemplated herein is configured to be coupleable with a cautery end effector that can operate as either a bipolar or monopolar cautery tool.

The magnetic ring 86 is made up of at least one magnet, and the ring is configured to rotate around the lumen 80. The end effector 50 is rotated via the magnetic interaction of the magnetic collar 58 on the end effector 50 and the magnetic ring 86 on the forearm 52. That is, the motor 102 in the forearm 52 can be actuated to drive the drive gear 98, which drives the driven gear 96, which is operably coupled to the magnetic ring 86 such that the magnetic ring 86 is rotated. The magnetic ring 86 is magnetically coupled to the magnetic collar 58 such that rotation of the magnetic ring 86 causes the magnetic collar 58 to rotate, thereby rotating the end effector 50. That is, the magnetic coupling of the magnetic ring 86 in the forearm 52 and the magnetic collar 58 on the end effector 50 can cause the rotation of the end effector 50 without a physical connection between the end effector 50 and the forearm 52.

In addition, the end effector 50 is actuated such that the grasper 54 moves between an open position and a closed position via the linear drive component 92. The end effector 50 is coupled to the linear drive component 92 via the coupling fingers 66, which are positioned around the drive component 92 and into a slot 108 defined in the drive component 92 as shown in FIGS. 3A and 3B. That is, the fingers 66 extend proximally beyond the proximal end of the central rod 68 and thus the proximal ends of the fingers 66 can be positioned into the slot 108 as shown. The coupling of the drive component 92 to the end effector 50 via the coupling fingers 66 results in the end effector 50 being linearly coupled to the linear drive component 92 such that the end effector 50 cannot move linearly in relation to the drive component 92. On the other hand, the coupling fingers 66 do allow the end effector 50 to rotate in relation to the drive component 92. That is, the fingers 66 are configured to allow for rotation of the fingers 66 in relation to the linear drive component 92 while not allowing for linear movement of the fingers 66 in relation to the linear drive component 92 when the fingers 66 are positioned in the slot 108 as shown in FIG. 3B. Alternatively, instead of coupling fingers 66, the coupling component 66 consists of any one or more mechanisms or components that are configured to be positioned within the slot 108 as described herein to couple the drive component 92 to the end effector 50.

As a result, the actuation of the linear drive component 92 causes the end effector 50 to be actuated to move linearly. That is, as discussed above, the threaded shaft 94 is threadably coupled at its proximal end to a drive cylinder 95 that can be actuated to cause the threaded shaft 94 to move axially. More specifically, the drive cylinder 95 is operably coupled to a drive gear (not shown) that is operably coupled to a motor (not shown) that can be actuated to rotate the drive gear and thereby rotate the drive cylinder 95. The rotation of the drive cylinder 95 causes the threaded shaft 94 to move axially via the threaded connection between the drive cylinder 95 and the threaded shaft 94. The threaded shaft 94 is configured such that it cannot be rotated. That is, the threaded shaft 94 has a slot 97 defined longitudinally in the shaft 94 such that a projection (also referred to as a "tongue" or "key") (not shown) coupled to the forearm 52 can be positioned in the slot 97, thereby preventing the threaded shaft 94 from rotating while allowing the threaded shaft 94 to move axially. The linear drive component 92 is coupled to the threaded shaft 94 such that rotation of the drive cylinder 95 causes the threaded shaft 94 to move axially, thereby causing the linear drive component 92 to move axially. Thus, actuation of the drive cylinder 95 by the motor (not shown) causes linear movement of the threaded shaft 94 and the linear drive component 92, thereby causing linear movement of the central rod 68, which results in the moving of the grasper 54 between an open configuration and a closed configuration via known grasper components for accomplishing the movement between those two configurations.

The end effector 50 is configured to be easily coupled to and uncoupled from the forearm 52 such that a user (such as a surgeon) can easily remove and replace one end effector with another during a medical procedure. As shown in FIG. 3A, the end effector 50 has been inserted into the lumen 80 but is not yet fully coupled to the forearm 52. That is, in FIG. 3A, the end effector 50 has been inserted into the lumen 80 such that the central rod 68 is in contact with the linear drive component 92 and the coupling fingers 66 have been positioned in the slot 108 of the drive component 92, but the coupler 56 has not yet been coupled to the projection 84. Note that, in this position (in FIG. 3A), the slidable cylinder 62 is in its retracted position.

In FIG. 3B, the coupler 56 has been coupled to the projection 84, thereby coupling the end effector 50 to the forearm 52 for use. That is, the urging of the coupler 56 proximally toward the forearm 52 urges the entire end effector 50 proximally toward the forearm. However, the disk 60 on the end effector 50 was already in contact with the shoulder 80B in the lumen 80 in FIG. 3A, so the disk 60 is restrained by the shoulder 80B from moving any further into the lumen 80 when the coupler 56 is urged proximally toward the forearm. Thus, the central rod 68, which is directly coupled to the disk 60 such that the rod 68 cannot move linearly in relation to the disk 60, also is restrained from moving any further into the lumen 80. However, the cylinder 62, which can move linearly in relation to the disk 60 (because the disk 60, as explained above, is seated in a tab 76 that is slidably positioned in the slot 78 in the cylinder 62), moves proximally toward the forearm due to the urging of the coupler 56 proximally. This causes the proximal end of the cylinder 62 to move proximally over the coupling fingers 66, which are positioned in the slot 108, as best shown in FIG. 3B. The result is that the cylinder 62 is positioned at least partially over the slot 108, thereby securing the fingers 66 in the slot 108, which thereby secures the end effector 50 to the forearm 52. This also causes the tension spring 70 disposed in the cylinder 62 to be compressed, because it is positioned between a shoulder 110 in the cylinder and tabs 112 at the distal end of the fingers 66. That is, the proximal advancement of the cylinder 62 as described above causes the shoulder 110 to move proximally toward the tabs 112 on the fingers 66, thereby causing the spring 70 to be compressed as shown.

It is understood that the end effector 50 can also be removed just as easily. First, the coupler 56 is pulled distally away from the forearm 52, thereby uncoupling the coupler 56 from the projection 84 as best shown in FIG. 3A. This removes the restraint placed on the end effector 50, thereby allowing the compressed spring 70 as shown in FIG. 3B to urge the cylinder 62 distally toward the grasper 54. This causes the proximal end of the cylinder 62 to move distally away from the linear drive component 92 and specifically from the slot 108, thereby freeing the proximal end of the fingers 66 from their position in the slot 108, as best shown in FIG. 3A. With the fingers 66 released from the slot 108, the end effector 50 can be removed from the lumen 80 of the forearm 52.

It is understood that the end effector 50 can be either bipolar or monopolar. Similarly, any of the other end effector embodiments disclosed or contemplated herein can also be either bipolar or monopolar, except as discussed in detail below with respect to the end effectors 260, 262 depicted in FIGS. 6-15.

FIGS. 4A-4D depict another embodiment of a magnetic coupling forearm 150, to which a quick-release, magnetically-coupled end effector (not shown) can be attached, according to one embodiment. In this embodiment, the forearm body 150 has two sets of magnets (in contrast to one set of magnets in the previous embodiment shown in FIGS. 2-3B). The first magnetic ring 152 is positioned at the distal end of the forearm 150 and drives rotation of the end effector (not shown), while the second magnetic ring 154 is positioned at the proximal end of the forearm 150 and drives linear actuation of the end effector (not shown), thereby actuating operation of the end effector. For example, in those embodiments in which the end effector (not shown) is a grasper, the second magnetic ring 154 would actuate opening and closing of the grasper. Both magnetic rings 152, 154 are each made up of at least one magnet. More specifically, in this exemplary embodiment, the first ring 152 is made up of six magnets 156, while the second ring 154 is also made up of six magnets 158. Alternatively, each of the rings 152, 154 is made up of at least one magnet. In a further alternative, the number of magnets in each ring 152, 154 can range from 1 to as many magnets that can fit in the ring to accomplish the purposes described herein.

Further, like the previous embodiment (above), the forearm body 150 has an end effector lumen 160 defined by a fluidically impervious tube 162 such that the lumen 160 is fluidically or hermetically sealed, thereby fluidically sealing the internal components of the forearm 150 from any fluids present in the lumen 160. The tube 162 is positioned in the lumen 160 such that the tube 162 defines the lumen 160. The lumen 162 contains two contact rings 164, 166.

Each ring 152, 154 is configured to rotate around the lumen 160 and thereby actuate the end effector (not shown) as described above. More specifically, the first magnetic ring 152 is caused to rotate and thereby cause a magnetic collar (not shown) or other magnetic component on the end effector (not shown) to rotate via the magnetic coupling between the ring 152 and the collar (not shown), thereby causing the end effector (not shown) to rotate. Further, the second magnetic ring 154 is caused to rotate and cause a second magnetic collar (not shown) or other magnetic component on the end effector (not shown) to rotate via the magnetic coupling between the two components, thereby actuating the end effector to operate.

Each of the contact rings 164, 166 is positioned around the wall of the tube 162 of the lumen 160 such that each ring 164, 166 encircles the lumen 160. In this embodiment, each of the contact rings 164, 166 is positioned along the length of the lumen 160 such that each is in contact with one contact component on the end effector (not shown). For example, if an end effector similar to the end effector 50 discussed above and depicted in FIG. 2 were used, the rings 164, 166 would be positioned to contact the leaf springs (64, not shown) of that end effector 50. Alternatively, the rings 164, 166 can be configured to contact any contact component on the end effector that is coupled to the forearm 150. Regardless, the contact rings 164, 166 make it possible to transmit electrical energy from power sources to the rings 164, 166 and on to the end effector in a fashion similar to that described above with respect to end effector 50. As a result, any end effector used with the forearm 150 can be a bipolar cautery tool or, alternatively, can be a monopolar cautery tool if the same electrical energy is supplied to both contact rings 164, 166.

The first magnetic ring 152 is actuated by a first motor 180, which is operably coupled to a drive gear 182, which is operably coupled to a driven gear 184, which is operably coupled to the first magnetic ring 152. Thus, actuation of the first motor 180 actuates the first magnetic ring 152 to rotate. Similarly, the second magnetic ring 154 is actuated by a second motor 190, which is operably coupled to a drive gear 192, which is operably coupled to a driven gear 194, which is operably coupled to the second magnetic ring 154. Thus, actuation of the second motor 180 actuates the second magnetic ring 154 to rotate.

Thus, in this embodiment, the forearm 150 actuates an end effector (not shown) entirely by magnetic couplings, rather than mechanical couplings. The first magnetic ring 152 rotates the end effector (not shown) via the magnetic interaction between the ring 152 and the corresponding magnetic collar (not shown) or other magnetic component on the end effector (not shown), while the second magnetic ring 154 actuates the end effector (not shown) via the magnetic interaction between the ring 154 and the corresponding magnetic collar (not shown) or other magnetic component on the end effector (not shown).

Hence, the forearm 150 is configured to allow for easy coupling and removal of an end effector (not shown), such that a user (such as a surgeon) can easily remove and replace one end effector with another during a medical procedure.

Figure 5A:
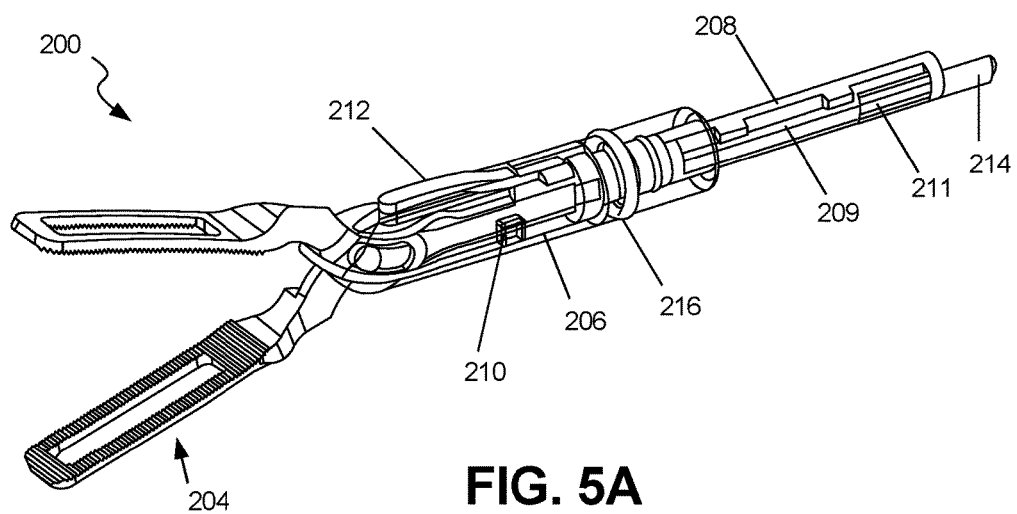
FIG. 5A is a perspective view of another quick-release end effector, according to a further embodiment.
Figure 5B:
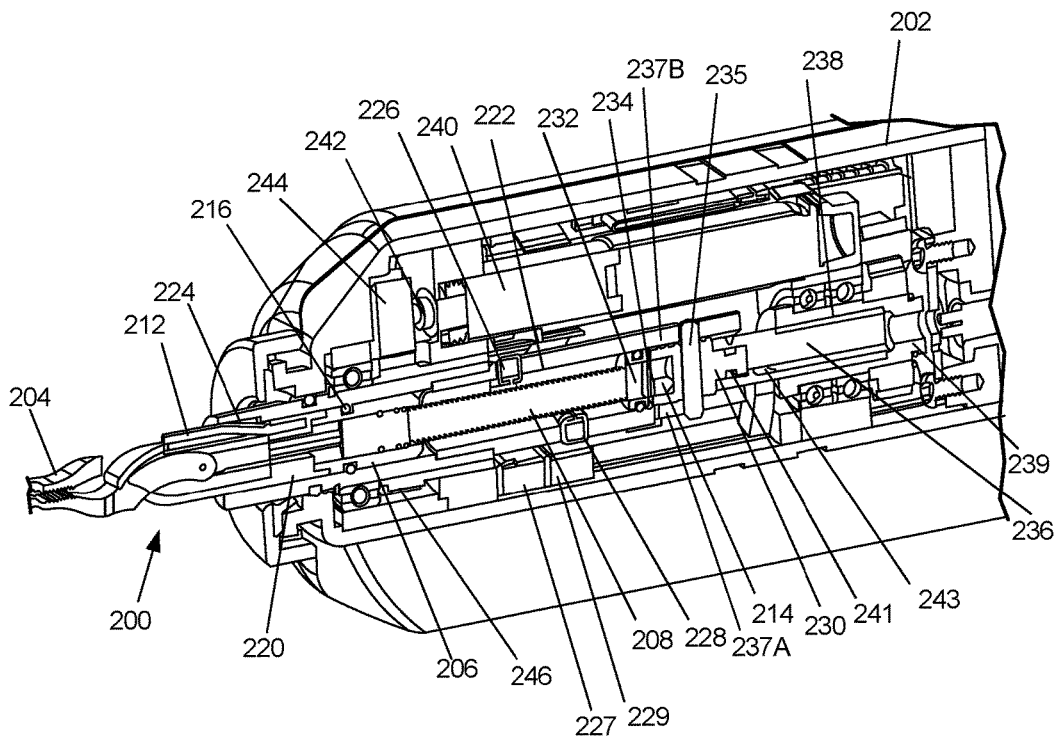
FIG. 5B is an expanded cross-sectional perspective view of a portion of the quick-release end effector of FIG. 5A positioned in a portion of a forearm, according to one embodiment.

FIGS. 5A and 5B depict another implementation of a quick-release end effector 200 that is releaseably coupleable to a forearm 202, according to one embodiment. More specifically, this exemplary implementation is configured to allow for coupling the end effector 200 to the forearm 202 with a single ninety degree turn of the end effector 200 once the end effector 200 is positioned within the lumen 220 of the forearm 202. This embodiment does not utilize magnetic coupling.

As best shown in FIG. 5A, the end effector 200 in this implementation has a grasper 204. The end effector 200 also has a tubular body 206, a rod (also referred to as a "central rod") 208 that is disposed within, is slidable in relation to, and extends proximally from the tubular body 206, two protrusions (the first protrusion 210 is depicted in FIG. 5A and a second protrusion is not shown), a release button 212, a coupling hook 214 at a proximal end of the central rod 208, and an o-ring 216 disposed around the tubular body 206. In addition, the rod 208 has two contact elements (also referred to as "contact strips") 209, 211 that are electrically coupled to the blades of the grasper 204 via separate wires or other connection components such that one strip 209 is coupled to one blade and the other strip 211 is coupled to the other blade. The central rod 208 is operably coupled to the grasper 204 such that linear actuation of the central rod 208 in relation to the tubular body 206 causes the grasper 204 to move between its open and closed configurations. The first 210 and second (not shown) protrusions are positioned on opposite sides of the tubular body 206 and are configured to be positioned within corresponding channels in the forearm 202 as described below.

The forearm body 202 has an end effector lumen 220 defined by a rotatable cylinder 222 such that the cylinder 222 defines the lumen 220. The cylinder 222 has a button channel 224 defined in the cylinder 222 to accommodate the release button 212 when the end effector 200 is positioned within the lumen 220, and two contact rings 226, 228. In addition, the cylinder 222 has two longitudinal channels (not shown) defined on opposite sides of the inner wall of the lumen 220 that are configured to receive the first protrusion 210 (as shown in FIG. 5A) and the second protrusion (not shown) on the end effector 200 such that the protrusions 210 move along the channels as the end effector 200 is inserted into the lumen 220 of the forearm 202. Further, the channels (not shown) both include a substantially ninety degree turn at the proximal end of the channels that results in two axial slots in communication with the longitudinal channels. The axial slots are configured to accommodate the rotation of the end effector 200 as it is coupled to the forearm 202 as described below.

Each of the contact rings 226, 228 is positioned on the cylinder 222 such that a portion of each ring 226, 228 is positioned around the inner wall of the cylinder 222 such that each ring encircles the lumen 220. In this embodiment, each of the contact rings 226, 228 is positioned along the length of the lumen 220 such that each is in contact with one of the two contact strips 209, 211 on the rod 208 when the end effector 200 is coupled to the forearm 202 as shown in FIG. 5B. More specifically, the contact ring 226 contacts contact strip 209 while contact ring 228 contacts contact strip 211. In this configuration, once the end effector 200 is coupled to the forearm 202, the contact strips 209, 211 are continuously in contact with the contact rings 226, 228, even when the rod 208 is rotating or moving axially. That is, the strips 209, 211 are configured to have some longitudinal length as shown in FIG. 5A such that when the rod 208 is actuated to move axially while coupled to the forearm 202, the strips 209, 211 remain in contact with the contact rings 226, 228 despite the fact that the rings 226, 228 do not move axially.

Further, each of the contact rings 226, 228 is in contact with a stationary contact ring 227, 229 disposed in the forearm 202 such that they encircle the cylinder 222. In addition to being positioned such that a portion is disposed around the inner wall of the cylinder 222, each of the rings 226, 228 also has a portion that is disposed around the external wall of the cylinder 222 such that each ring 226, 228 contacts one of the two stationary contact rings 227, 229 as well. Thus, electrical energy can be transmitted from the power sources to the stationary contact rings 227, 229 and—via the contact between the stationary rings 227, 229 and the contact rings 226, 228—to the contact strips 209, 221 and thereby to the grasper 204 blades. As a result, the grasper 204 can be a bipolar cautery tool. Alternatively, the end effector 200 can also be a monopolar cautery tool if the same electrical energy is supplied to both stationary contact rings 227, 229.

In addition, the forearm 202 has a linear drive component 230 disposed in a proximal end of the rotatable cylinder 222. The drive component 230 has a lumen 232 defined in its distal end, and the lumen 232 has a coupling pin (also referred to as a "hook coupling pin") 234 extending from one side of the lumen 232 to the other. The pin 234 is configured to be coupleable with the coupling hook 214 of the end effector 200 as will be described in further detail below. Further, the drive component 230 also has a coupling pin (also referred to as a "cylinder coupling pin") 235 that extends beyond the outer circumference of the drive component 230 such that the ends of the pin 235 are positioned in slots 237A, 237B defined in the inner wall of the rotatable cylinder 222. The pin 235 is fixedly coupled to the drive component 230. Each of these slots 237A, 237B has a length that extends longitudinally along the length of the rotatable cylinder 222. As a result, this pin 235 is slidably positioned in the slots 237A, 237B such that the drive component 230 can be moved linearly but cannot rotate in relation to the rotatable cylinder 222. Thus, any rotation of the drive component 230 causes rotation of the rotatable cylinder 222. This configuration prevents the hook 214 from becoming decoupled from the pin 234. That is, the pin 235 prevents the drive component 230 from rotating in relation to the rotatable cylinder 222, thereby ensuring the hook 214 remains coupled to the pin 234.

Further, the proximal end of the drive component 230 has an externally threaded proximal shaft (also referred to as a linear translation component) 236. Alternatively, the shaft 236 is a separate component operably coupled to the drive component 230, via a retaining ring 241. The retaining ring 241 results in the drive component 230 being capable of rotating in relation to the linear translation component 236. Further, the shaft 236 is prevented from rotating by a groove (not shown) defined in the shaft 236 that mates with a tongue 243. In addition, the shaft 236 is positioned within a lumen 238 in a rotatable linear drive component 239 and is threadably coupled to the internal threads defined in the lumen 238. Thus, when the rotatable drive component 239 is rotated by the linear actuation motor (not shown), the threaded connection of the shaft 236 to the rotatable drive component 239 causes the shaft 236 to move linearly, thereby resulting in the drive component 230 moving linearly as well.

The forearm 202 also has a motor 240 coupled to a drive gear 244 via a drive shaft 242. The drive gear 244 is coupled to a driven gear 246 that encircles and is coupled to the rotatable cylinder 222 such that rotation of the driven gear 246 causes the rotatable cylinder 222 to rotate.

The end effector 200 is rotated via the motor 240 that is operably coupled to the driven gear 246. That is, the motor 240 in the forearm 202 can be actuated to drive the drive gear 244, which drives the driven gear 246, which is operably coupled to the rotatable cylinder 222 as described above such that the rotatable cylinder 222 is rotated. The rotatable cylinder 222 is coupled to the end effector 200 when the end effector 200 is fully seated in the lumen 220 of the forearm 202 such that rotation of the rotatable cylinder 222 causes the end effector 200 to rotate. That is, as best shown in FIG. 5A, the first protrusion 210 and second protrusion (not shown) are positioned in the channels (not shown) in the lumen 220 such that the tubular body 206 is coupled to the cylinder 222 such that the tubular body 206 rotates when the cylinder 222 rotates.

In addition, the end effector 200 is actuated such that the grasper 204 moves between an open position and a closed position via the linear drive component 230. The end effector 200 is coupled to the linear drive component 230 via the coupling hook 214, which is positioned into the lumen 232 of the drive component 230 and around the pin 234 positioned in the lumen 232. That is, during insertion of the end effector 200 into the forearm 202, the hook 214 is positioned into the lumen 232 prior to the substantially ninety degree rotation of the end effector 200 such that the hook 214 extends proximally past the pin 234. Thus, when the end effector 200 is rotated, the hook 214 couples to the pin 234 and thereby couples the end effector 200 to the drive component 230. The coupling of the drive component 230 to the end effector 200 via the hook 214 and pin 234 results in the end effector 200 being linearly coupled to the linear drive component 230 such that the end effector 200 cannot move linearly in relation to the drive component 230.

As a result of the coupling of the hook 214 to the pin 234, the actuation of the linear drive component 230 causes the end effector 200 to be actuated to move linearly. That is, the rotatable linear drive component 239 is coupled at its proximal end to a driven gear 250 that is coupled to a drive gear (not shown), which is coupled to a motor (not shown) that can be actuated to rotate the driven gear 250 and thus the rotatable drive component 239. As discussed above, the threaded section 236 of the linear drive component 230 is positioned in and threadably connected with the lumen 238 in the rotatable drive component 239. As a result, rotation of the drive component 239 causes the linear drive component 230 to move axially. Thus, actuation of the drive component 239 by the motor (not shown) causes linear movement of the linear drive component 230, thereby causing linear movement of the central rod 208, which results in the moving of the grasper 204 between an open configuration and a closed configuration via known grasper components for accomplishing the movement between those two configurations.

The end effector 200 is configured to be easily coupled to and uncoupled from the forearm 202 such that a user (such as a surgeon) can easily remove and replace one end effector with another during a medical procedure. To insert the end effector 200 into the forearm 202 and couple it thereto as shown in FIG. 5B, the end effector 200 is inserted into the lumen 220 such that the first protrusion 210 and second protrusion (not shown) are positioned in the channels (not shown) in the lumen 220. As the end effector 200 is urged proximally into the lumen 220, the hook 214 will advance proximally until it moves into the lumen 232 and past the pin 234. When the hook 214 can advance proximally no farther, the protrusions 212 (and not shown) are also advanced as far proximally as possible along the channels (not shown). At this point, the user rotates the end effector 200, thereby coupling the hook 214 to the pin 234 and advancing the protrusions 212 (and not shown) along the axial slots described above. Thus, a user can couple the end effector 200 to the forearm 202 via two mechanisms with a single twist or rotation of the end effector 200.

It is understood that the end effector 200 can also be easily removed. The release button 212 on the end effector 200 is operably coupled to the coupling hook 214 such that actuation of the button 212 causes the hook 214 to uncouple from the pin 234. Thus, to remove the end effector 200 from the forearm 202, a user can depress the button 212 and then rotate or twist the end effector 200 (in the opposite direction of that required to couple the end effector 200). The rotation of the end effector 200 moves the protrusions 212 (and not shown) along the axial slots (not shown) so that the protrusions 212 (and not shown) are positioned in the channels (not shown) such that they can move distally along the channels (not shown). At this point, the end effector 200 can be removed from the lumen 220 of the forearm 202.

FIGS. 6-14 depict certain additional embodiments of quick-release end effectors 260, 262 that are releaseably coupleable to a forearm 264, according to one embodiment. More specifically, these exemplary implementations are configured to allow for coupling of the end effector 260, 262 to the forearm 264 with a single turn of the end effector 260, 262 once the end effector 260, 262 is positioned within the lumen 300 of the forearm 264.

Figure 6:
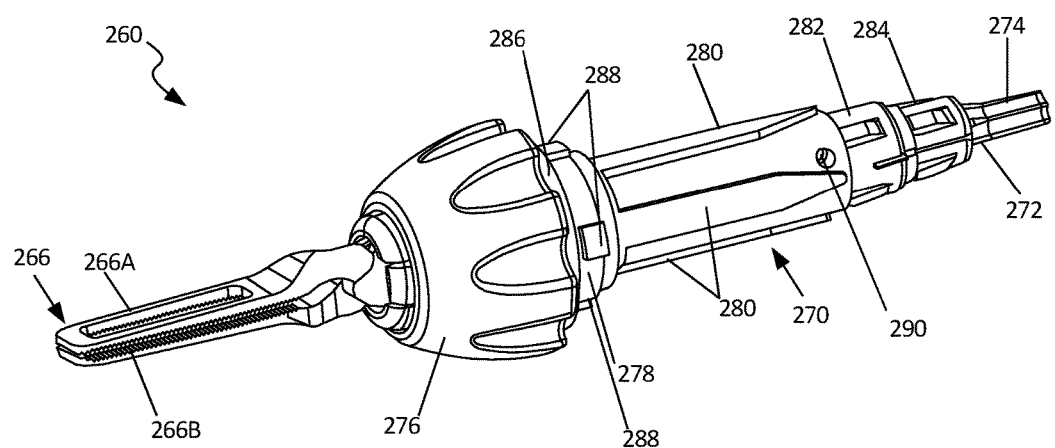
FIG. 6 is a perspective view of another quick-release end effector, according to yet another embodiment.
Figure 14:
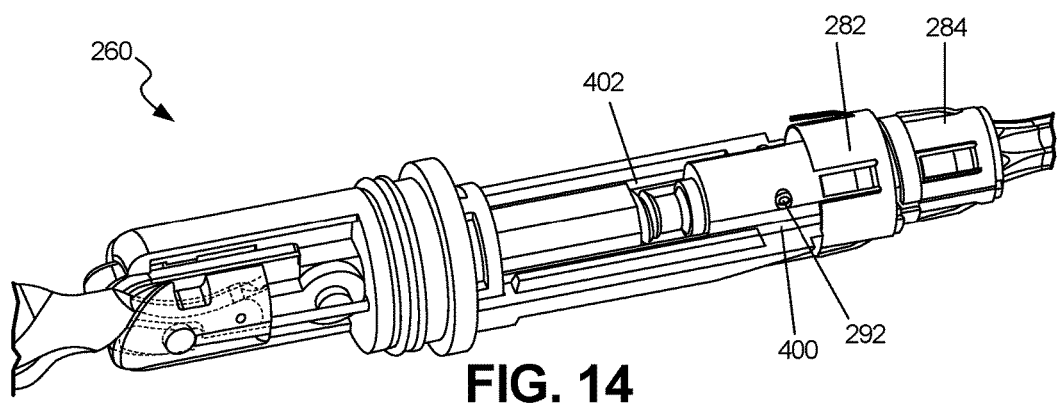
FIG. 14 is an expanded perspective view of the quick-release end effector of FIG. 6 with certain components removed for easier viewing of certain portions of the end effector.

As shown in FIGS. 6 and 14, the end effector 260 in one implementation has a grasper 266. The end effector 260 also has a tubular body 270, a rod (also referred to herein as a "central rod") 272 that is disposed within and is rotatable in relation to the tubular body 270 and has a rod coupling component 274 that extends proximally from the tubular body 270, a handle 276, an end effector coupling component 278, torque transfer protrusions 280, two contact rings 282, 284, an o-ring 286 adjacent to the handle 276, and a pin hole 290 defined in the tubular body 270. Further, as best shown in FIG. 14, the first contact ring 282 is coupled to a first contact wire 400 that extends from the contact ring 282 to the distal end of the end effector 260, where the wire 400 is operably coupled to a proximal portion of one arm 266A of the grasper 266. Similarly, the second contact ring 284 is coupled to a second contact wire 402 that extends from the ring 284 to the distal end of the end effector 260, where the wire 402 is operably coupled to a proximal portion of the other arm 266B of the grasper 266. Thus, each of the two contact rings 282, 284 is electrically coupled to one of the grasper arms 266A, 266B such that electrical energy can be separately transferred from each of the rings 282, 284 to one of the arms 266A, 266B, thereby resulting in a bipolar grasper 266. The central rod 272 is operably coupled to the grasper 266 such that rotational actuation of the central rod 272 (via the rod coupling component 274) in relation to the tubular body 270 causes the grasper 266 to move between its open and closed configurations. The end effector coupling component 278 has male protrusions 288 that mate with female channels 380 on the forearm such that protrusions 288 can be positioned into the channels 380 and the end effector 260 can be coupled to the forearm 264 with a single twist or rotation of the end effector 260. The torque transfer protrusions 280 are formed or positioned around the tubular body 270 and are configured to be positioned within corresponding torque transfer channels 304 in the forearm 264 as described below such that the end effector 260 is not rotatable in relation to the forearm 264 when the protrusions 280 are seated in the channels 304. Note that the ends of the torque transfer protrusions 280 are tapered to make it easier to align the protrusions 280 with the channels 304. In the embodiment of FIG. 6, there are four protrusions 280 (with three visible in the figure). Alternatively, there can be any other number of protrusions that can be used to couple the end effector 260 to the forearm 264, including one to three protrusions, or five or more protrusions.

Figure 7:
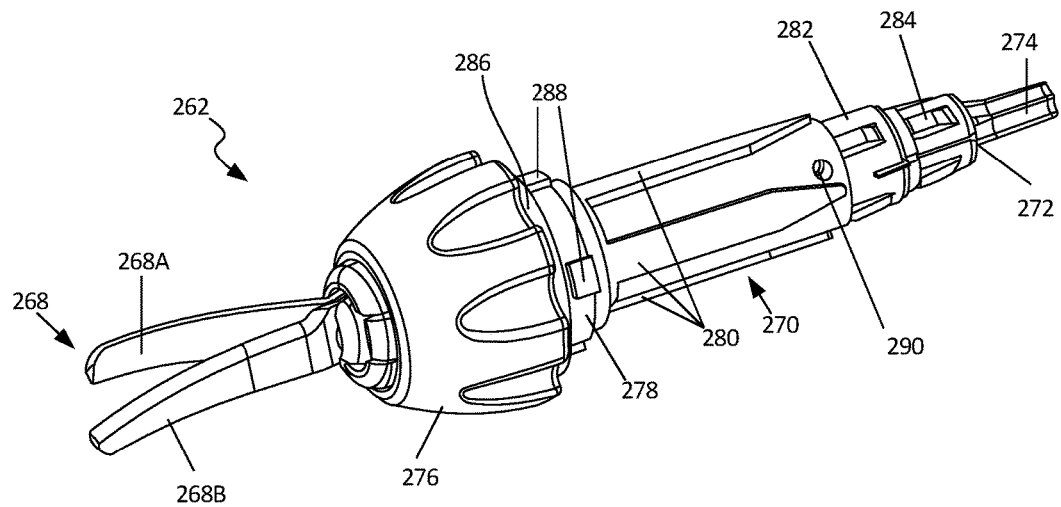
FIG. 7 is a perspective view of another quick-release end effector, according to another embodiment.
Figure 15:
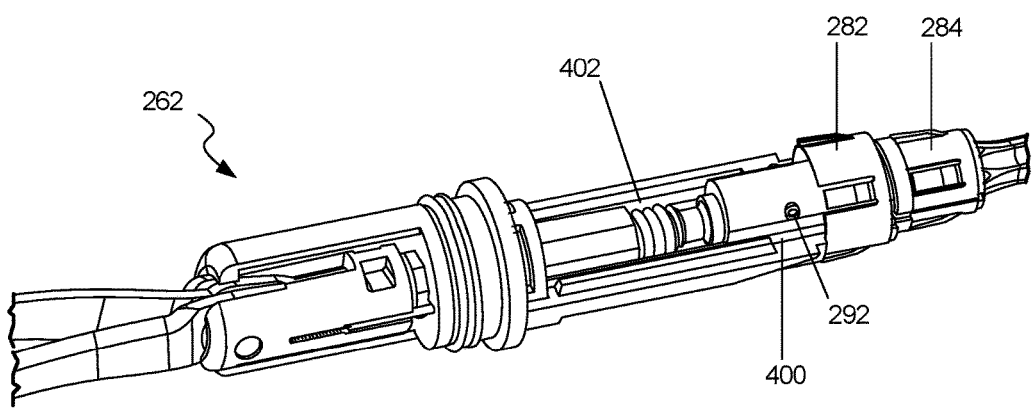
FIG. 15 is an expanded perspective view of the quick-release end effector of FIG. 7 with certain components removed for easier viewing of certain portions of the end effector.

In an alternative embodiment, the end effector 262 can have a pair of scissors 268 as shown in FIG. 7. According to one implementation, the other components of this end effector 262 are substantially the same as those of the end effector 260 depicted in FIG. 6 and discussed above. As such, those components are identified with the same reference numbers such that the discussion above applies equally to these components as well. One difference, in certain embodiments, relates to the electrical coupling of the contact rings 282, 284 to the scissor arms 268A, 268B. That is, according to some embodiments, both arms 268A, 268B are electrically coupled to both rings 282, 284, thereby resulting in a monopolar pair of scissors 268 as will be described in further detail below. More specifically, as best shown in FIG. 15, the first contact ring 282 is coupled to a first contact wire 400 that extends from the contact ring 282 to the distal end of the end effector 262, where the wire 400 is operably coupled to a proximal portion of the pair of scissors 268 such that the contact ring 282 is electrically coupled to both arms 268A, 268B of the pair 268. Similarly, the second contact ring 284 is coupled to a second contact wire 402 that extends from the ring 284 to the distal end of the end effector 262, where the wire 402 is operably coupled to a proximal portion of the pair of scissors 268 such that the contact ring 284 is electrically coupled to both arms 268A, 268B of the pair 268. Thus, each of the two contact rings 282, 284 is electrically coupled to both scissor arms 268A, 268B such that electrical energy is transferred from both rings 282, 284 to both arms 266A, 266B, thereby resulting in a monopolar grasper 268.

Figure 8:
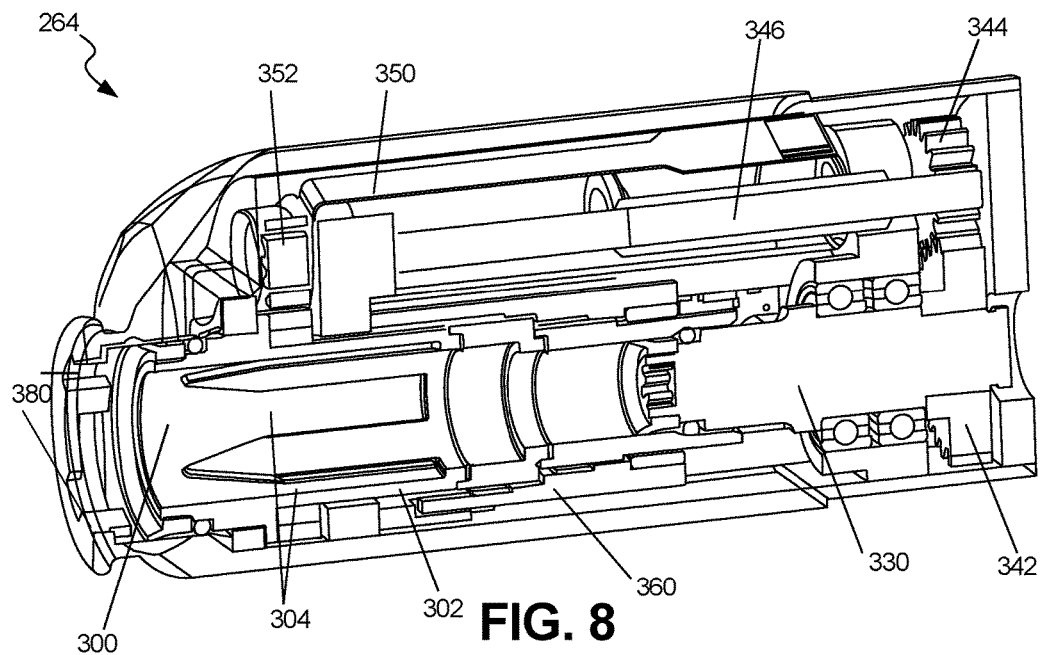
FIG. 8 is a cross-sectional side view of another quick-release forearm configured to receive a quick-release end effector, according to another embodiment.
Figure 9A:
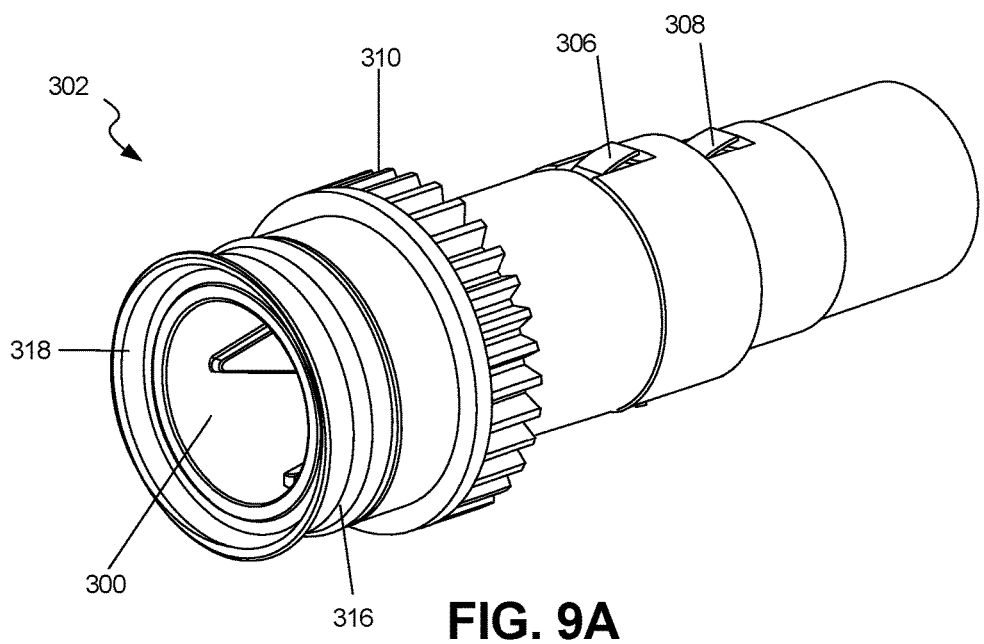
FIG. 9A is a perspective view of a rotatable cylinder that can define the end effector lumen in the quick-release forearm of FIG. 8, according to one embodiment.
Figure 9B:
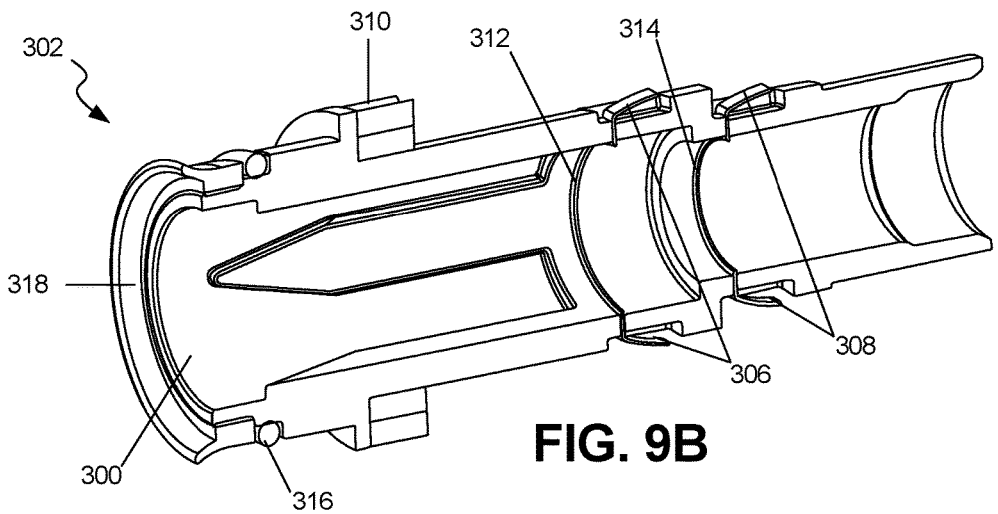
FIG. 9B is a cross-sectional perspective view of the rotatable cylinder of FIG. 9A.

As shown in FIGS. 8-13, the forearm body 264 has an end effector lumen 300 defined by a rotatable cylinder 302 (as best shown in FIGS. 8, 9A, and 9B) such that the cylinder 302 defines the lumen 300. As mentioned above, the cylinder 302 has torque transfer channels 304, two electrical contact components 306, 308, a rotational gear 310 defined or positioned around an external wall of the cylinder 302, an o-ring 316 disposed around the cylinder, and a seal (a "ring seal" or "lip seal" in this embodiment) 318 disposed around the distal opening of the lumen 300. The torque transfer channels 304 are defined in the cylinder 302 to accommodate the torque transfer protrusions 280 of either end effector 260/262 when that end effector 260/262 is positioned within the lumen 300. The channels 304 are tapered to make it easier to align the protrusions 280 with the channels 304. In this exemplary embodiment, the two electrical contact components 306, 308 are contact leaflets 306, 308 that are electrically coupled to contact rings 312, 314 (as best shown in FIG. 9B) (such that the electrical contact component 306 is coupled to the contact ring 312 and contact component 308 is coupled to the contact ring 314). The contact rings 312, 314 are disposed along the inner wall of the lumen 300 and are positioned along the length of the lumen 300 such that they are configured to be in contact with the contact rings 282, 284 on the end effector 260/262 when the end effector 260/262 is coupled to the forearm 264. In one embodiment as shown in FIG. 9B, the contact leaflet pair 306, 308 extend away from the cylinder 302 in the proximal direction. Alternatively, it is understood that the contact leaflets 306, 308 can extend away from the cylinder 302 in the distal direction. In a further alternative, the contact components 306, 308 can each have any known configuration for a contact component.

As best shown in FIGS. 9A and 9B, the lip seal 318 operates to serve as the primary seal to retain the fluidic seal of the forearm 264, thereby preventing fluid from accessing the forearm 264. The o-ring 316 (as also best shown in FIGS. 9A and 9B), according to one embodiment, can operate to serve as a structural support with respect to the cylinder 302, retaining the cylinder 302 in position in relation to the forearm 264 while allowing the cylinder 302 to rotate. In addition, the o-ring 316 can also operate as a backup to the lip seal 318, thereby providing a fluidic seal that prevents any fluid that gets past the lip seal 318 from accessing the internal components of the forearm 264. Further, according to another implementation, the o-ring 316 can also serve to retain lubricant disposed between the lip seal 318 and the o-ring 316.

Alternatively, instead of seal 318, which extends from the rotatable cylinder 302, the seal (not shown) for retaining the fluidic seal of the forearm 264 can instead extend from an inner lumen of the forearm 264—such as a portion of the forearm 264 proximal to the female channels 380—and contact the rotatable cylinder 302, thereby providing the desired fluidic seal for the forearm 264 as described above.

Figure 10:
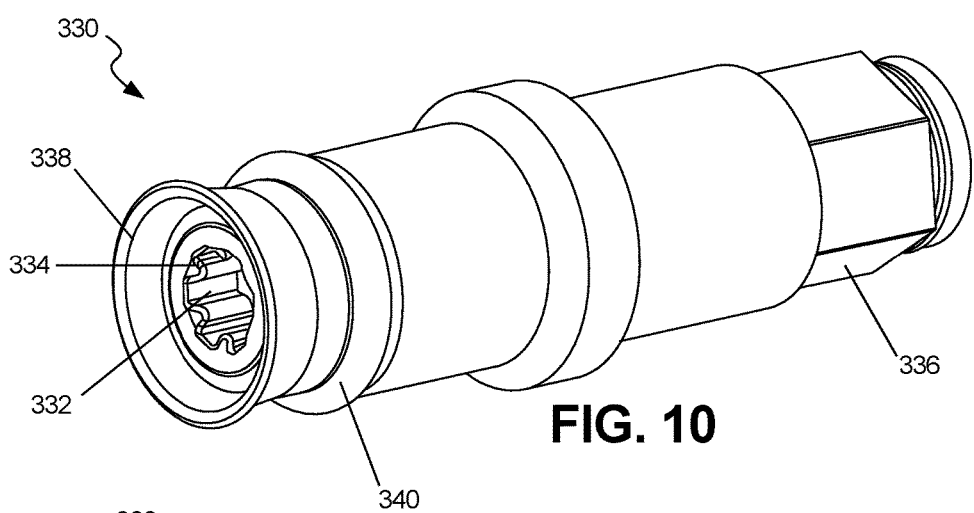
FIG. 10 is a perspective view of a linear drive component that can be positioned in the quick-release forearm of FIG. 8, according to one embodiment.

In addition, the forearm 264 has a rotatable linear drive component 330 disposed in the forearm 264 proximally to the rotatable cylinder 302, as best shown in FIGS. 8 and 10. The drive component 330 has a lumen 332 defined in its distal end (as best shown in FIG. 10), and the lumen 332 has teeth 334 extending from the inner wall of the lumen 332 that are configured to mate with the rod coupling component 274 on the proximal end of the end effector 260/262. Alternatively, the lumen 332 can have any type of structure or mechanism—such as ribs, threads, channels, or the like—for mating with or coupling to the rod coupling component 274. In addition, the drive component 330 has an external structural feature 336, a seal 338 (such as a "ring seal"), and an o-ring 340. The ring seal 338 and o-ring 40, according to one embodiment, can function in substantially the same fashion as the seal 318 and o-ring 316 discussed above. The external structural feature 336 is an external hexagon 336 as best shown in FIG. 10 that is configured to mate with a driven gear 342 operably coupled with a drive gear 344 that is operably coupled with a motor 346 (as best shown in FIG.

8) such that actuation of the motor 346 causes the rotation of the rotatable drive component 330.

Alternatively, instead of ring seal 338, which extends from the linear drive component 330, the seal (not shown) for retaining the fluidic seal can instead extend from the lumen 300 of the rotatable cylinder 302 and contact the rotatable linear drive component 330, thereby providing the desired fluidic seal.

Figure 12:
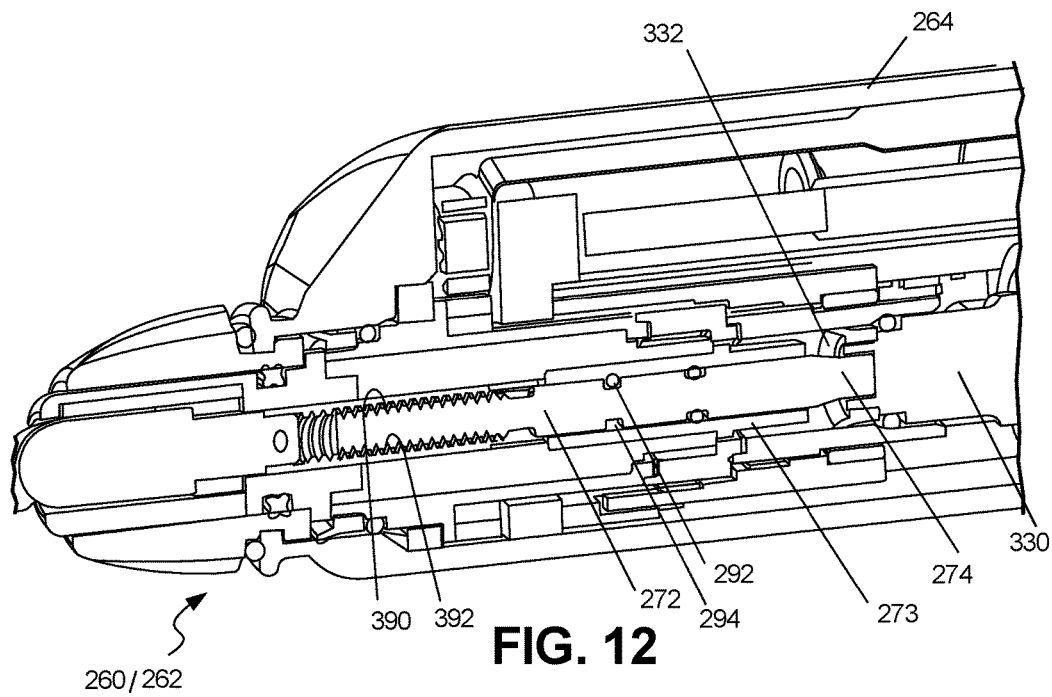
FIG. 12 is a cross-sectional side view of the quick-release forearm of FIG. 8 with a quick-release end effector positioned therein, according to one embodiment.

When the end effector 260/262 is coupled to the forearm 264 as best shown in FIGS. 12, the rod coupling component 274 of the end effector 260/262 is positioned within the lumen 332 of the drive component 330 and thereby coupled to the rotatable drive component 330. As a result of this coupling, when the rotatable drive component 330 is rotated, the rod coupling component 274 is caused to rotate, thereby rotating the central rod 272 of the end effector 260/262. The central rod 272 is disposed within housing 273 and has a slot 294 defined around the outer circumference of the rod 272 that is configured to receive the pin 292, which is best shown in FIGS. 12, 14, and 16. The pin 292 is positioned through the pin hole 290 in the tubular body 270 as best shown in FIGS. 6 and 7. As best shown in FIG. 12, the pin 292 is positioned in the slot 294 such that the rod 272 can rotate but cannot move axially when the pin 292 is in the slot 294. Alternatively, instead of a pin, the housing 273 has a protrusion similar to the pin 292 that extends from an inner lumen of the housing 273 such that the protrusion can be positioned in the slot 294 in a fashion similar to the pin 292, thereby allowing the rod 272 to rotate but not move axially. The central rod 272 has an externally threaded section 390 on its distal end which threadably couples with a linear drive component 392 such that rotation of the central rod 272 causes the linear drive component 392 to move linearly. The linear drive component 392 is operably coupled to the grasper 266 or pair of scissors 268 such that linear movement of the drive component 392 causes the grasper 266 or pair of scissors 268 to move between open and closed configurations. Thus, the rotation of the central rod 272 causes the grasper 266 or pair of scissors 268 to move between open and closed positions.

Returning to FIG. 8, in accordance with one implementation, the forearm 264 also has a motor 350 coupled to a drive gear 352. The drive gear 352 is coupled to the rotational gear 310 on the rotatable cylinder 302 (as best shown in FIG. 9A) such that rotation of the drive gear 352 causes the rotatable cylinder 302 to rotate. The rotatable cylinder 302 is coupled to the end effector 260/262 when the end effector 260/262 is fully seated in the lumen 300 of the forearm 264 such that rotation of the rotatable cylinder 302 causes the end effector 260/262 to rotate. That is, the protrusions 280 are positioned in the channels 304 in the lumen 300 such that the tubular body 270 is coupled to the cylinder 302 such that the tubular body 270 rotates when the cylinder 302 rotates.

Figure 11:
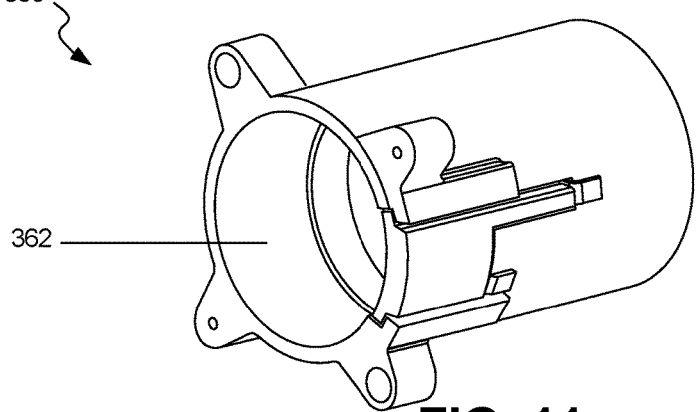
FIG. 11 is a perspective view of a support cylinder that can be positioned around the rotatable cylinder in the quick-release forearm of FIG. 8, according to one embodiment.
Figure 13:
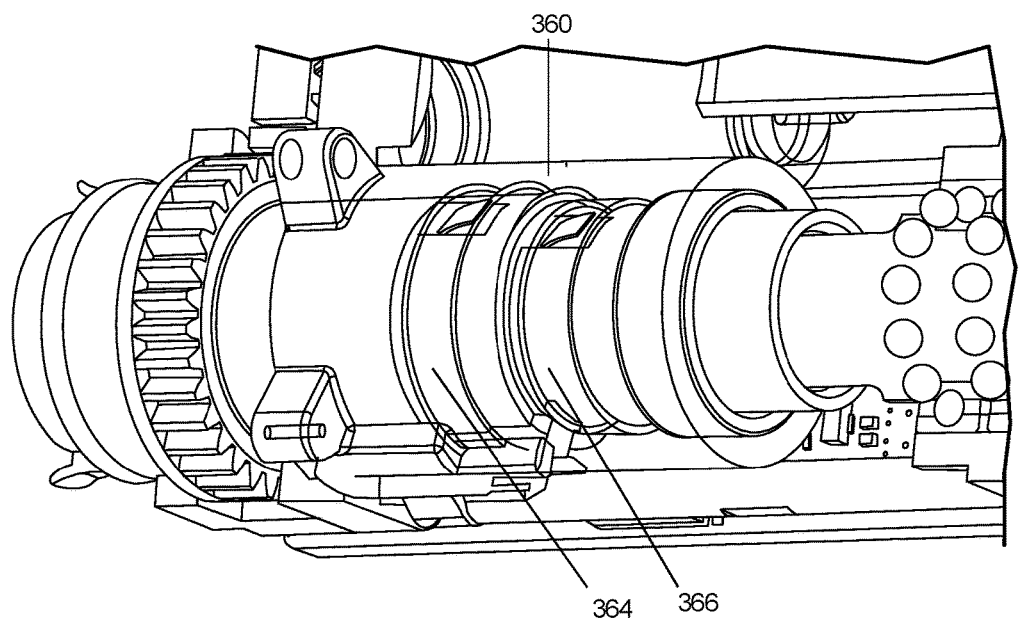
FIG. 13 is an expended perspective view of the quick-release forearm of FIG. 8 with certain components removed for easier viewing of certain portions of the forearm.

In one embodiment as best shown in FIGS. 8, 11, and 13, the forearm 264 also has a support cylinder 360 positioned around the rotatable cylinder 302 and having a lumen 362 such that the rotatable cylinder 302 can be positioned in the lumen 362 and rotate in relation to the support cylinder 360. As best shown in FIG. 13, the support cylinder 360 (shown in dotted lines) has two inner contact rings 364, 366 disposed on the inner wall of the support cylinder lumen 362. The two rings 364, 366 are configured to be in contact with the two contact leaflet pairs 306, 308 on the rotatable cylinder 302.

As best shown in FIGS. 8 and 12, both of the end effectors 260, 262 are configured to be easily coupled to and uncoupled from the forearm 264 such that a user (such as a surgeon) can easily remove and replace one end effector with another during a medical procedure. To insert either end effector 260/262 into the forearm 264 and couple it thereto as shown in FIG. 12, the end effector 260/262 is inserted into the lumen 300 such that the torque transfer protrusions 280 are positioned in the channels 304 in the lumen 300. As the end effector 260/262 is urged proximally into the lumen 300, the rod coupling component 274 will advance proximally until it is positioned in the lumen 332 of the rotatable drive component 330 and mates with the teeth 334 therein. At the same time, the proximal advancement of the end effector 260/262 causes the male protrusions 288 on the end effector coupling component 278 to advance proximally into the female channels 380 defined in the distal end of the forearm 264, as best shown in FIG. 8. The female channels 380 are configured such that once the protrusions 288 have been advanced proximally into the channels 380, the end effector 260/262 can be rotated via the handle 276 by a user to cause the protrusions 288 to rotate in the channels 288, thereby securing the end effector 260/262 to the forearm 264. Thus, a user can couple the end effector 260/262 to the forearm 264 with a single twist or rotation of the end effector 260/262. Further, the user can also remove the end effector 260/262 in the same fashion by simply twisting or rotating the handle 276 in the opposite direction.

In one implementation, any lumen in any forearm device described or contemplated herein is configured to be easy to sterilize. That is, each lumen is configured to have no crevices or other features that are inaccessible or difficult to access during sterilization. Further, certain embodiments have lumens that have dimensions that make for easy sterilization. That is, such lumens have a length that is sufficiently short and a diameter that is sufficiently large to be accessible by appropriate sterilization tools and techniques. In one specific example, any one or more of the lumens disclosed or contemplated herein can have an inside diameter of at least 3 mm and a length of 400 mm or shorter. Alternatively, the lumen(s) can have an inside diameter of at least 2 mm and a length of 250 mm or shorter. In a further alternative, the lumen(s) can have an inside diameter of at least 1 mm and a length of 125 mm or shorter. In yet another alternative, the lumen(s) can have any dimensions that simplify sterilization.

According to certain embodiments, the various forearm and end effector embodiments disclosed or contemplated herein provide for easy, quick coupling and uncoupling of the end effector to the forearm while providing for one or even two mechanical couplings or interfaces and one or two electrical couplings or interfaces. That is, the various embodiments disclosed herein allow for simple attachment of an end effector to a forearm while also providing up to two electrical couplings and up to two mechanical couplings between the forearm and the end effector.

Although the various embodiments have been described with reference to preferred embodiments, persons skilled in the art will recognize that changes may be made in form and detail without departing from the spirit and scope of the invention.

What is claimed is:

1. An arm component for a medical device, the arm component comprising:
   (a) an arm body;
   (b) a rotatable cylinder disposed within the arm body, the rotatable cylinder comprising:
       (i) an end effector lumen defined within the rotatable cylinder; and (ii) at least one torque transfer channel defined in a wall of the end effector lumen such that the least one torque transfer channel extends longitudinally along the wall from a distal end of the end effector lumen; and
(c) a rotatable linear drive component operably coupled to the rotatable cylinder, the linear drive component comprising:
(i) a rotatable body; and
(ii) a drive component lumen defined in a distal portion of the rotatable body, wherein the drive component lumen comprises mating features defined within the drive component lumen.

2. The arm component of claim 1, further comprising a ring seal disposed between the arm body and the rotatable cylinder, whereby the ring seal is configured to prevent fluid from accessing the arm body.

3. The arm component of claim 1, further comprising a first motor operably coupled to a first drive gear, wherein the first drive gear is operably coupled to an external gear disposed on an outer wall of the rotatable cylinder, wherein actuation of the first motor causes rotation of the rotatable cylinder.

4. The arm component of claim 1, further comprising a second motor operably coupled to a second drive gear, wherein the second drive gear is operably coupled to a driven gear operably coupled to the linear drive component, wherein actuation of the second motor causes rotation of the linear drive component.

5. The arm component of claim 1, further comprising:
(a) a first outer contact ring disposed around the rotatable cylinder;
(b) a second outer contact ring disposed around the rotatable cylinder;
(c) a first contact component disposed on an outer wall of the rotatable cylinder such that the first contact component is in continuous contact with the first inner contact ring regardless of a rotational position of the rotatable cylinder;
(d) a second contact component disposed on the outer wall of the rotatable cylinder such that the second contact component is in continuous contact with the second inner contact ring regardless of the rotational position of the rotatable cylinder;
(e) a first inner contact ring disposed on the inner wall of the end effector lumen; and
(f) a second inner contact ring disposed on the inner wall of the end effector lumen.

6. The arm component of claim 5, further comprising a quick-release end effector configured to be positionable within the end effector lumen, the quick-release end effector comprising first and second end effector contact components, wherein the first end effector contact component is in contact with the first inner contact ring and the second end effector contact component is in contact with the second inner contact ring when the quick-release end effector is operably coupled to the arm.

7. The arm component of claim 1, further comprising a quick-release end effector configured to be positionable within the end effector lumen, the quick-release end effector comprising:
(a) an end effector body;
(b) at least one torque transfer protrusion defined in an exterior portion of the end effector body, wherein the at least one torque transfer protrusion is configured to be mateable with the at least one torque transfer channel in the end effector lumen;
(c) a rod disposed within the end effector body; and
(d) a rod coupling component disposed at a proximal portion of the rod, wherein the rod coupling component is configured to be coupleable with the mating features defined in the lumen of the rotatable linear drive component.

8. A quick-release end effector for a medical device, the end effector comprising:
(a) an end effector body;
(b) an end effector coupling component disposed around the end effector body, the end effector coupling component comprising at least one male protrusion extending from the coupling component;
(c) at least one torque transfer protrusion defined in an exterior portion of the end effector body;
(d) a rod disposed within the end effector body;
(e) a rod coupling component disposed at a proximal portion of the rod, the rod coupling component comprising first mating features disposed on an external portion of the rod coupling component; and
(f) first and second contact rings disposed around the rod.

9. The quick-release end effector of claim 8, further comprising an end effector disposed at a distal end of the end effector body, wherein the end effector is operably coupled to the rod such that actuation of the rod causes actuation of the end effector.

10. The quick-release end effector of claim 8, further comprising a grasper end effector comprising first and second grasper arms, wherein the first contact ring is electrically coupled to the first grasper arm and the second contact ring is electrically coupled to the second grasper arm.

11. The quick-release end effector of claim 8, wherein the end effector body is configured to be positionable in a lumen of an arm of a medical device.

12. The quick-release end effector of claim 8, wherein the end effector body is configured to be positionable in a lumen of an arm of a medical device, the lumen comprising at least one torque transfer channel defined in the lumen, wherein the at least one torque transfer protrusion is configured to be mateable with the at least one torque transfer channel in the end effector lumen.

13. The quick-release end effector of claim 8, wherein the end effector body is configured to be positionable in a lumen of an arm of a medical device, wherein the arm comprises at least one female channel defined in a distal portion of the arm, wherein the end effector coupling component is configured to be coupleable to the arm such that the at least one male protrusion is mateable with the at least one female channel.

14. The quick-release end effector of claim 8, wherein the end effector is configured to be positionable in an arm of a medical device, wherein the arm comprises:
(a) an arm body;
(b) a rotatable cylinder disposed within the arm body, the rotatable cylinder comprising:
(i) an end effector lumen defined within the rotatable cylinder; and
(ii) at least one torque transfer channel defined in a wall of the end effector lumen; and
(c) a rotatable linear drive component operably coupled to the rotatable cylinder, the linear drive component comprising:
(i) a rotatable body; and
(i) a lumen defined in a distal portion of the rotatable body, wherein the lumen comprises second mating features defined within the lumen, wherein the first mating features of the rod coupling component are configured to be coupleable with the second mating features defined within in the lumen of the rotatable linear drive component.

* * * * *